United States Patent [19]

Gourvest et al.

[11] Patent Number: 5,086,047
[45] Date of Patent: Feb. 4, 1992

[54] NOVEL STEROIDS

[75] Inventors: Jean-Francois Gourvest, Joinville le Pont; Dominique Lesuisse, Paris, both of France

[73] Assignee: Roussel Uclaf, Department des Brevets, Romainville, France

[21] Appl. No.: 633,291

[22] Filed: Dec. 24, 1990

[30] Foreign Application Priority Data

Dec. 22, 1989 [FR] France .................. 89 17047

[51] Int. Cl.$^5$ .................. A61K 31/56; C07J 17/00; C07J 1/00; C07J 9/00; C07J 7/00; C07J 31/00; C07J 4/00; C07J 11/00

[52] U.S. Cl. .................. 514/177; 540/114; 552/519; 552/520; 552/523; 552/526; 552/530; 552/531; 552/540; 552/543; 552/544; 552/548; 552/552; 552/553; 552/554; 552/555; 552/557; 552/599; 552/604; 552/605; 552/607; 552/608; 552/610; 552/611; 552/650; 552/651; 552/632

[58] Field of Search ............... 552/553, 604, 605, 607, 552/608, 531, 530, 632, 610, 611, 650, 651, 599, 519, 520, 543, 544, 548, 552, 540, 555, 554, 557, 523, 526; 514/177; 540/114

[56] References Cited

U.S. PATENT DOCUMENTS 4,634,694 1/1987 Loozen et al. .................. 552/632
5,030,627 7/1991 Kloosterboer et al. .................. 552/520

FOREIGN PATENT DOCUMENTS 0289450 2/1988 European Pat. Off. ............. 552/632

Primary Examiner—Glennon H. Hollrah
Assistant Examiner—Kimberly J. Kestler
Attorney, Agent, or Firm—Bierman and Muserlian

[57] ABSTRACT

A compound selected from the group consisting of a compound of the formula

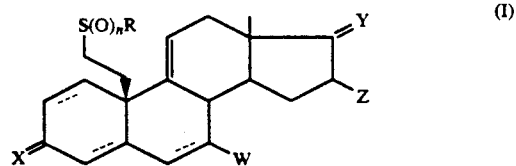

wherein R is selected from the group consisting of hydrogen, alkyl, alkylthio and haloalkyl of 1 to 6 carbon atoms, alkenyl and alkynyl of 2 to 6 carbon atoms, optionally substituted arylthio of 6 to 10 carbon atoms, aryl of 6 to 12 carbon atoms, acyl of an organic carboxylic acid of 1 to 12 carbon atoms, —CN, cycloalkyl of 3 to 6 carbon atoms and —(CH$_2$)$_m$—Re, m is an integer from 1 to 3, Re is —OH or —SH or —Salk, Alk is alkyl of 1 to 6 carbon atoms, X is selected from the group consisting of oxygen, N—O—R$_1$, or =X is H$_2$ or

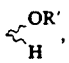

R$_A$ and R$_B$ are individually selected from the group consisting of hydrogen, halogen and alkyl of 1 to 6 carbon atoms, R$_1$ is hydrogen or alkyl of 1 to 6 carbon, R' is hydrogen or acyl, the wavy lines indicate —or -position, Y is selected from the group consisting of oxygen, NOR$_1$,

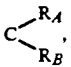

or =Y is

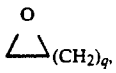

H$_2$ and

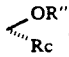

q is an integer from 1 to 3, Rc is selected from the group consisting of hydrogen, alkyl of 1 to 6 carbon atoms and alkenyl and alkynyl of 2 to 6 carbon atoms, R" is hydrogen or acyl W is selected from the group consisting of hydrogen, optionally substituted alkyl and alkylthio of 1 to 6 carbon atoms and optionally substituted arylthio of 6 to 10 carbon atoms, Z is hydrogen or alkyl of 1 to 10 carbon atoms, n is an integer from 0 to 2, the dotted lines in 1(2)-, 4(5)- and 6(7)-position indicate an optional double bond between the carbon atoms and their nontoxic, pharmaceutically acceptable salts having aromatase specific activity.

12 Claims, No Drawings

NOVEL STEROIDS

STATE OF THE ART

Related prior art includes U.S. Pat. No. 4,495,102 and U.S. Pat. No. 4,096,254.

The observation according to which approximately 35% of breast cancers are estrogen-dependent has led to research into ways of limiting the production of estrogens. After having using surgical methods consisting of suppressing the sources of estrogens (ovaries) or the sources of their biosynthetic precursors, the androgens (suprarenal glands), the development of less traumatizing methods has been sought. [ABUL-HAJJ., Steroid Biochem, Vol. 13 (1980), p. 1935; BRODIE, Cancer Res., Vol. 42, (1982), p. 3312].

In this respect, the specific inhibition of the last enzymatic stage of the aromatization of 3-keto-$\Delta^4$ androgens into phenolic estrogens appears to be the most effective and least disturbing method. The enzyme responsible for this conversion is a mono-oxy-genase known as being a cytochrome P450 : AROMATASE (BRODIE, J. Endocrinol, Invest., Vol. 2 (1979), p. 445) which requires oxygen and NADPH (Reduced form of Nicotinamide Adenine Dinucleotide Phosphate) to effect the aromatization of androgens into estrogens.

Based on another mechanism, other authors (for example, MARCOTTE et al, Biochemistry, Vol. 21, (1982), p. 2773, FLYNN et al, Biochem. Biophys. Res. Com., Vol. 103, (1981), p. 713) have proposed suicide inhibitors for Aromatase. Competitive inhibitors such as Aminogluthetimide have also been proposed in the treatment of metastatic breast cancers. This product however has been shown as not being specific to Aromatase. In fact, it attacks enzymatic processes other than that which leads from androgens to estrogens.

OBJECTS OF THE INVENTION

It is an object of the invention to provide the novel compounds of formula I and their non-toxic, pharmaceutically acceptable salts and a novel process and intermediates for the preparation thereof.

It is another object of the invention to provide novel compositions and method for including aromatase specific activity in warm-blooded animals.

These and other objects and advantages of the invention will become obvious from the following detailed description.

THE INVENTION

The novel compounds of the invention are selected from the group consisting of a compound of the formula

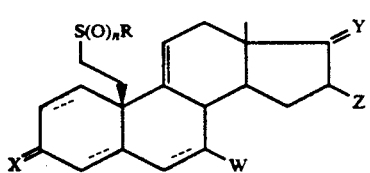

(I)

wherein R is selected from the group consisting of hydrogen, alkyl, alkylthio and haloalkyl of 1 to 6 carbon atoms, alkenyl and alkynyl of 2 to 6 carbon atoms, optionally substituted arylthio of 6 to 10 carbon atoms, aryl of 6 to 12 carbon atoms, acyl of an organic carboxylic acid of 1 to 12 carbon atoms, —CN, cycloalkyl of 3 to 6 carbon atoms and —(CH$_2$)$_m$—Re, m is an integer from 1 to 3, Re is —OH or —SH or —SAlk, Alk is alkyl of 1 to 6 carbon atoms, X is selected from the group consisting of oxygen, N—O—R$_1$,

or =X is H$_2$ or a

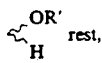

R$_1$ is hydrogen or alkyl of 1 to 6 carbon atoms, R$_A$ and R$_B$ are individually selected from the group consisting of hydrogen, halogen and alkyl of 1 to 6 carbon atoms, R' is hydrogen or acyl, the wavy lines indicate α- or β-position, Y is selected from the group consisting of oxygen, NOR$_1$,

or =Y is

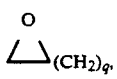

H$_2$ and

q is an integer from 1 to 3, Rc is selected from the group consisting of hydrogen, alkyl of 1 to 6 carbon atoms and alkenyl and alkynyl of 2 to 6 carbon atoms, R" is hydrogen or acyl W is selected from the group consisting of hydrogen, optionally substituted alkyl and alkylthio of 1 to 6 carbon atoms and optionally substituted arylthio of 6 to 10 carbon atoms, Z is hydrogen or alkyl of 1 to 10 carbon atoms, n is an integer from 0 to 2, the dotted lines in 1(2)-, 4(5)- and 6(7)-position indicate an optional double bond between the carbon atoms and their non-toxic, pharmaceutically acceptable salts.

Examples of alkyl are methyl, ethyl, propyl, isopropyl, butyl, isobutyl, secondary butyl, tert-butyl, pentyl and hexyl and examples of alkenyl and alkynyl are vinyl, allyl, 1-propenyl, ethynyl and 1- or 2-propynyl. Examples of haloalkyl are alkyl mono- or pluri-substituted by halogens such as fluorine, chlorine, bromine, iodine. By pluri-substituted is meant especially di- or tri-halo substituted alkyl. Specific examples are monofluoro, chloro, bromo or iodomethyl, difluoro, dichloro or dibromomethyl, trifluoromethyl. Examples of alkylthio correspond to the alkyl mentioned above such as methylthio and ethylthio.

Examples of aryl are carbocyclic aryls such as phenyl or naphthyl or heterocyclic aryls with 5 or 6 links containing one or more heteroatoms chosen preferably from oxygen, sulfur and nitrogen. Among the heterocyclic aryls with 5 links are furyl, thienyl, pyrrolyl, thiazolyl, oxazolyl, imidazolyl, thiadiazolyl, pyrazolyl and isoxazolyl. Among the heterocyclic aryls with 6 links are pyridyl, pyrimidinyl, pyridazinyl and pyrazinyl. Among the condensed aryls are indolyl, benzofurannyl, benzothienyl and quinolinyl.

The arylthios correspond to the aryls mentioned above for example phenylthio non-substituted or substituted by at least one amino or nitro.

Among the halogen atoms are fluorine, chlorine, bromine or iodine. Among the cycloalkyls of 3 to 6 carbon atoms are cyclopropyl, cyclobutyl, cyclopentyl or cyclohexyl.

Among the acyls of the organic carboxylic acids are acyl of an aliphatic or cycloaliphatic acid, saturated or unsaturated, and notably the acyl of an alkanoic acid such as acetic acid, propionic acid, butyric acid, isobutyric acid, valeric acid or undecylic acid, the acyl of a hydroxyalkanoic acid such as hydroxyacetic acid, the acyl of a cycloalkylcarboxylic or (cycloalkyl) alkanoic acid such as cyclopropyl, cyclopentyl or cyclohexyl carboxylic acid, cyclopentyl or cyclohexyl acetic acid or propionic acid, the acyl of a benzoic acid or phenylalkanoic acid such as phenyl acetic acid or phenyl propionic acid, the acyl of an amino acid such as diethylamino acetic acid or aspartic acid or the acyl of formic acid. Acetyl, propionyl or benzoyl are preferred.

By acylated hydroxy is meant preferably an alkanoyloxy derivative of an alkanoic acid as defined above or $$-O-\underset{\underset{O}{\|}}{C}-(CH_2)_p-CO_2H$$

in which p is a number from 2 to 5.

Preferred examples of R are methyl, ethyl, acetyl, fluoromethyl, difluoromethyl, methylthio, vinyl, allyl, and ethynyl. $R_1$ is preferably hydrogen or methyl. Among the products of formula I there are preferred the products in which R is other than hydrogen when X is not methylene.

A preferred group of compound have the formula

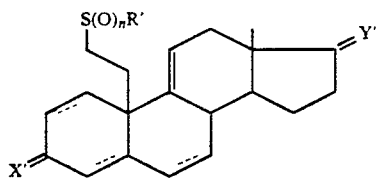

I' wherein R' is selected from the group consisting of alkyl, alkylthio and haloalkyl of 1 to 4 carbon atoms, alkenyl and alkynyl of 2 to 4 carbon atoms, —CH and acyl of an aliphatic carboxylic acid of 1 to 4 carbon atoms, X' is selected from the group consisting of O, $CH_2$ and $NOR'_1$ or =X' is

$R'_1$ is hydrogen or alkyl of 1 to 4 carbon atoms, Y' is O or =Y' is

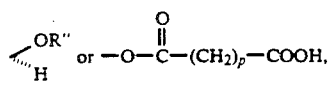

R'' is hydrogen or acyl of an alkanoic acid and p and the dotted lines have the above definitions.

Among the products of formula I' there are preferred the products in which R' is chosen from alkyl, alkenyl, alkynyl or haloalkyl of up to 4 carbon atoms and X' is oxygen or =X' is

Specific preferred compounds are 10β-[2-(methylthio)-ethyl]-Δ$^{4,9(11)}$-estradiene-3,17-dione; 10β-[2-(ethylthio)-ethyl]-Δ$^{4,9(11)}$-estradiene-3,17-dione; 10β-[2-(methylthio)-ethyl-Δ$^{4,9(11)}$-estradiene-17-ol-3-one; 10β-[2-(ethenylthio)-ethyl]-Δ$^{4,9(11)}$-estradiene-3,17-dione; 10β-[2-(ethynylthio)-ethyl]-Δ$^{4,9(11)}$-estradiene-3,17-dione; 10β-[2-(fluoromethylthio)-ethyl]-Δ$^{4,9(11)}$-estradiene-3,17-dione; the butane dioate of 10β-[2-(methylthio)-ethyl]-Δ$^{4,9(11)}$-estradien-3-one-17β-yl and of sodium; 10β-[2-(methylthio)-ethyl-Δ$^{4,9(11)}$-estradiene-3β, 17β-diol; 10β-[2-methylthio)-ethyl]-Δ$^{4,9(11)}$-estradiene-3, 17β-diol and 10β-[2-(methylthio)-ethyl-Δ$^{9(11)}$-estrene-3,17-dione.

The novel process of the invention for the preparation of the compounds of formula I comprises reacting a compound of the formula

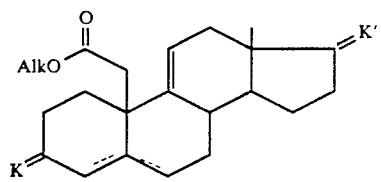

II in which K and K' individually are protected keto and Alk is alkyl of 1 to 4 carbon atoms, the dotted lines being a double bond in position 4(5) or 5(6) with a reducing agent to obtain a compound of the formula

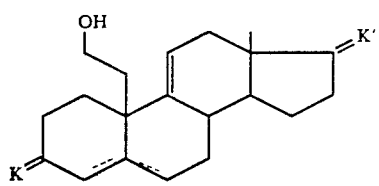

III which is treated, either with a transformation reagent of the hydroxy into a thiol to obtain a product of the formula

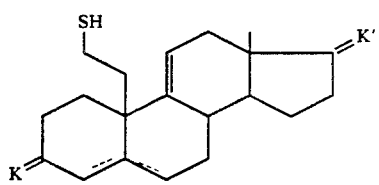

IV which is treated with a reactive derivative of R to obtain a product of the formula

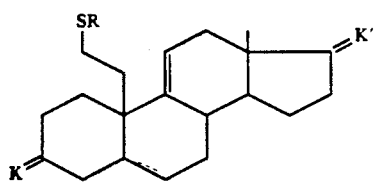

V or with a reactive derivative of a sulfonic acid to obtain a product of the formula

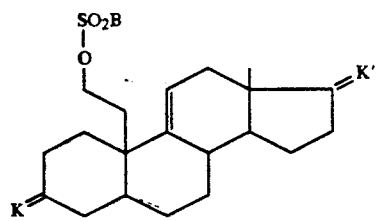

VI in which B is the acyl of a sulfonic acid, reacting the latter with a salt of the formula RSA in which A is a monovalent cation to obtain a product of formula V as defined above, which product is treated with a deprotection reagent of the protected ketone functions to obtain a product of the formula

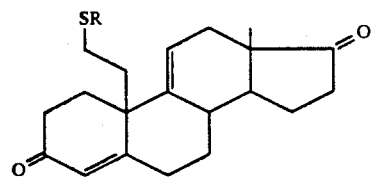

Ia corresponding to the products of formula I in which R has the meanings indicated above, X and Y each are oxygen, n is 0, and the dotted lines in position (4) 5 represent a double bond and the dotted lines in positions 1(2) and 6(7) do not represent a second bond between the carbons that carry them, which products of formula Ia are optionally subjected to one or more of the following reactions and in any order:
  introduction of a double bond in position 1(2)
  introduction of a double bond in position 6(7)
  oxidation of the sulfur atom of the -SR into sulfoxide or sulfone,
  selective reduction of the double bond in position 4(5)
  introduction of an alkyl in position 16
  introduction of an alkyl, alkylthio or arylthio optionally substituted in position 7 to obtain the products of the formula

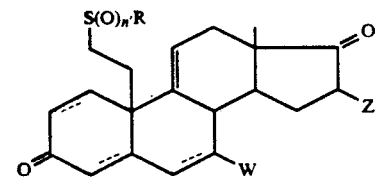

Ib in which n' is 1 or 2 and the dotted lines in position 1(2), 4(5) and 6(7) indicate the optional presence of a double bond between the carbons that carry them and corresponding to the products of formula I in which R has the meanings indicated above, X and Y each are oxygen and W, Z and n and the dotted lines in positions 1(2), 4(5) and 6(7) have the previous meanings, and optionally the products of formulae Ia and Ib are subjected to at least one of the following reactions in any order:
  introduction of a

in position 3 and/or 17, action of the hydroxylamine or of a derivative of the formula $H_2N{-}O{-}R_1$, reduction of the 3 and/or 17-ketone function and optional acylation of the hydroxy function then if desired salification of the esterified function, conversion of the 17 ketone into a

$(CH_2)_q$ group to obtain a product of the formula

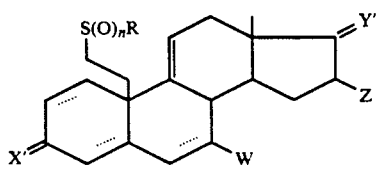

Ic in which n, R, W, Z and the dotted lines in positions 1(2), 4(5) and 6(7) have the meaning indicated above and X' and Y' have the values indicated above for X and Y except that least one of X or Y is not oxygen.

A variant of the process for the preparation of products of formula I comprises reacting a product of the formula

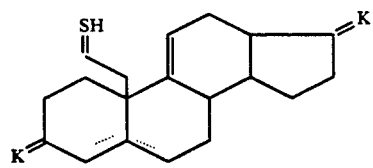

IV or

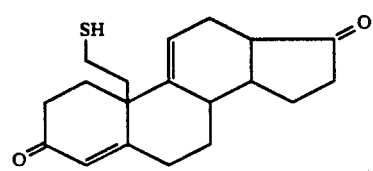

I'a as defined previously with a 4-dinitrophenylsulfenyl halide to obtain a product of the formula

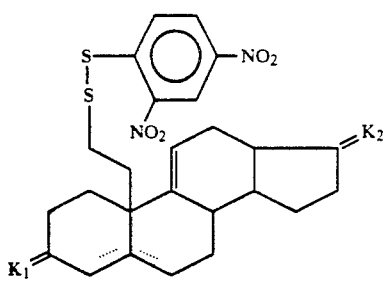

in which K₁ and K₂ are a ketone or a protected ketone, reacting the latter 1) either with a deprotection reagent of the 3- or 17-ketones to obtain a product of the formula

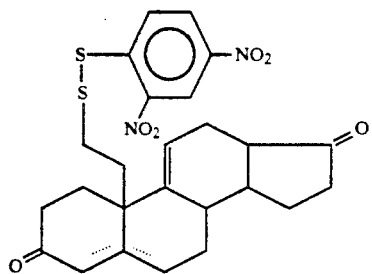

Id 2) or with an organo-magnesium compound reagent of the formula R'—Mg—Hal in which Hal is halogen and R" is alkyl, alkenyl, alkynyl, haloalkyl, aryl, —CN or —(CH₂)$_m$Re, or with a protected organo-lithium compound R"Li then to a deprotection agent of the R" then, if appropriate, to a deprotection reaction of the 3 and-/or 17-ketones to obtain a product of the formula

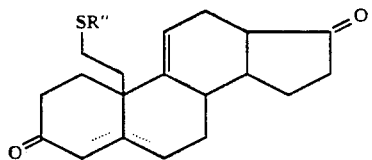

Ie in which R" has the meaning indicated above, 3) or with a salt of the formula R'"SA in which A has the above meaning and R'" is alkyl of 1 to 6 carbon atoms or an optionally substituted aryl of 6 to 10 carbon atoms, then if appropriate, to a deprotection reaction of the 3 and-/or 17-ketones to obtain a product of the formula

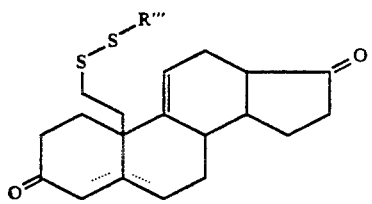

If and products of formulae Id, Ie, If are optionally subjected to one or more of the reactions indicated above for the products of formula Ia or Ib in any order.

A process for the preparation of the products of formula I in which =X and/or =Y is

VII comprises reacting a product of formula II as defined above with a reducing agent of the protected ketones to obtain a product of formula III in which =K and/or =K' is hydrogen and the synthesis is continued as indicated above.

In the preferred conditions for implementing the processes described above, the reduction of the products of formula II to obtain the products of formula III is carried out using a hydride, preferably lithium-aluminium hydride in an aprotic solvent such as tetrahydrofuran or ethyl ether, for example at ambient temperature. In the product of formula II, alk preferably is ethyl, the conversion reagent of the hydroxyl into a thiol is diethyl azodicarboxylate in the presence of triphenylphosphine and thioacetic acid whereby an intermediate product containing a 10β-acetylthioethyl, which is converted into a thiol by the action of hydrazine. The two stages of the reaction are preferably carried out in an aprotic solvent such as tetrahydrofuran or diethyl ether, The reactive derivative of the R that is preferably used is a halide such as chloride or bromide although a pseudo-halide can also be used such as a mesylate or a tosylate. The operation takes place in the presence of a strong base such as an alkali metal alcoholate, for example potassium tert-butylate, or an amide, for example lithium diisopropyl amide, or lithium or potassium hexamethyldisilylazanate. The operation can take place in a solvent such as tetrahydrofuran at low temperature i.e. between 0 and −78° C.

The reactive derivative of the sulfonic acid of the formula BSO₃H in which B is preferably methyl or tolyl is preferably a halide such as chloride and mesyl chloride is preferably used in the presence of a mineral or organic base, preferably triethylamine. A reaction solvent such as methylene chloride is used and the reaction is effected at a temperature on the order of 20° C.

The salt of formula RSA of R'"SA in which R and R'" have the above meaning is preferably an alkali metal salt such as sodium or lithium and is effected preferably in an aprotic solvent such as tetrahydroduran, hexamethylphosphoramide or dimethylformamide. The operation can be done in the presence of a specific crown ether of the metal used such as 12-crown-4 for lithium, 15-crown-5 for sodium, or 18-crown 6 for potassium. The action of the salt of formula RSA on the product of formula VI can lead to a partial or total deblocking of one or both of the ketone functions protected at function 3- and 17-positions. Notably a product of the formula

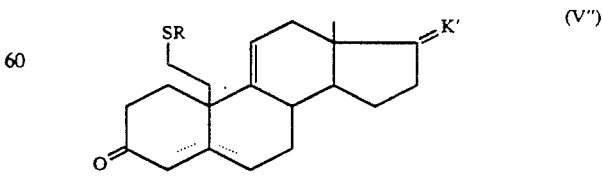

(V")

can be obtained, which can of course lead to the products of formula Ia under the same conditions as the products of formula V.

The hydrolysis of the products of formula V into products of formula Ia is preferably an acid hydrolysis, for example using concentrated hydrochloric acid (2 to 6N) or acetic acid in a solvent such as methanol, ethanol or tetrahydrofuran. The optional introduction of a double bond in position 1(2) is carried out by DDQ preferably in a solvent such as dioxane and the optional selective reduction of the $\Delta^4$ double bond is carried out with hydrogen in the presence of a catalyst with palladium in the presence of pyridine or an alkali metal, preferably lithium, in liquid ammonia. The optional introduction of a double bond in position 6(7) is carried out with an orthoformate such as ethyl orthoformate in the presence of p-toluene sulfonic acid in a standard solvent such as ethanol, which reaction is followed by that of chloranile in a solvent such as aqueous acetone.

The optional oxidation of the sulfur atom into sulfoxide is carried out by action of a periodate such as sodium periodate in an aqueous solvent such as aqueous methanol or of a peracid such as m-chloroperbenzoic acid in a solvent such as dichloromethane. The optional oxidation of this sulfur atom into sulfone is carried out with a peracid such as m-chloroperbenzoic acid and the optional introduction of

in position 3 or 17 is carried out using the so-called Wittig reaction in which a triphenylalkyl halide or a haloalkyl phosphonium is used, preferably bromide in the presence of a strong base such as butyl lithium or potassium tert-butylate. Dibromo difluoro methane and hexamethylphosphotriamide in the presence of triglyme can also be used.

The optional introduction of

in position 17 is carried out using an Rc-Li reagent in a solvent such as tetrahydrofuran after blocking of the ketone function in position 3 in the form of an enol ether. The action of the hydroxylamine or of one of its derivatives is carried out preferably in a solvent such as pyridine, or in the presence of a mineral base such as sodium bicarbonate in an aqueous solvent such as methanol.

The reduction of the 3- and/or 17-ketone is carried out using a hydride such as sodium borohydride in a solvent such as methanol, or lithium-aluminium hydride in a solvent such as tetrahydrofuran, or Raney nickel or also an alkali metal such as lithium in liquid ammonia. The optional acylation of the 3- or 17- hydroxyl is carried out using an acid derivative such as an acid anhydride or chloride preferably in the presence of a halohydric acid collector such as pyridine. The optional salification of the ester functions is carried out by the usual conditions, for example with a sodium salt such as sodium carbonate or sodium bicarbonate. The introduction of a 16-alkyl is carried out by the formation of an anion enolate in position 16 using a strong base such as lithium diisopropylamide or lithium hexamethyldisilylamide in a solvent such as tetrahydrofuran, then treatment with an alkyl halide such as an iodide.

The introduction of a 7-alkyl is carried out using an organomagnesium compound reagent alk-Mg-Hal in which alk is the alkyl to be introduced and Hal is halogen such as chlorine, bromine or iodine in the presence of a cuprous salt, preferably a halide. The introduction of a 7-alkylthio or arylthio is carried out using an alkyl or aryl mercaptan in a solvent such as tetrahydrofuran or dioxane in the presence of catalytic quantities of sodium. The cyclization reaction that leads to a product containing a

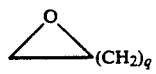

is carried out using a halide such as trimethylsulfonium iodide in the presence of dimethylsulfoxide and sodium hydride after blocking of the 3-ketone in the form of enol ether, for example. The protection of 3- or 17-ketone is carried out by the usual methods in of p-toluenesulfonic acid, in the form of dithio-ketal by using 1,2-ethane dithiol in the presence of p-toluenesulfonic acid or boron trifluoride etherate or in the form of enol ether by using an alkyl orthoformate such as ethyl orthoformate in the presence of p-toluenesulfonic acid. According to the type of protection used, a double bond can exist between carbons 4 and 5 or between carbons 5 and 6. The protection of the 3-keto in the form of enol ether gives rise to the obtaining of a system of $\Delta^{3,5}$ bonds.

The deprotection can be carried out by the usual methods, notably by acid hydrolysis as indicated for the products of formula V. When the protector group is a thioketal, a reduction is carried out preferably using Raney nickel or an alkali metal such as lithium in liquid ammonia. The organo-metallic reagent which is reacted with the product of formula IV or I'a is preferably a magnesium compound or a lithium compound. In the case where the group to be introduced contains a reactive function, this function can be protected by usual methods, for example by a trimethylsilyl remainder. The reaction is taken, according to usual methods, preferably to a temperature between $-100°$ C. and $0°$ C. The deprotection of the R'' can be brought about by tetraalkylammonium fluoride.

The compositions of the invention having aromatase specific activity (cytochrome P450 aromatase) comprises an effective amount of at least one compound of formula I and an inert pharmaceutical carrier or excipient. The compositions may be in the form of tablets, dragees, capsules, granules, suppositories, pessaries, ointments, creams, gels, patches and injectable preparations.

Examples of suitable excipients are talc, arabic gum, lactose, starch, magnesium stearate, cocoa butter, acqueous or non-aqueous vehicles, fatty substances of animal or vegetable origin, paraffin derivatives, glycols, various wetting, dispersing or emulsifying agents and preservatives.

The compositions due to their aromatase specific activity (cytochrome P450 aromatase) are useful for the treatment of cancers of the breast, endometrium, ovary and pancreas, gynecomastia, benign breast disorders, endometriosis, polycystic affections of the ovary and prostatic hyperplasia and more generally in the treatment of hyperestrogenemia.

The novel method of inducing aromatase specific activity in warm-blooded animals, including humans, comprises administering to warm-blooded animals an amount of a compound of formula I sufficient to induce aromatase specific activity. The compounds may be administered orally, rectally, topically or parenterally and the usual daily dose is 0.0066 to 0.133 mg/kg depending on the condition treated, the specific compound and the method of administration.

The novel intermediates of the invention are the compounds of formulae II, III, IV, V and VI. The compounds of formula II also possess aromatase inhibiting activity.

The compounds of formula II may be prepared subjecting a compound of the formula

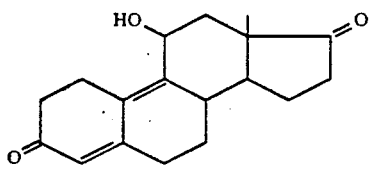
(A)

to a Claisen rearrangement to obtain a product of the formula

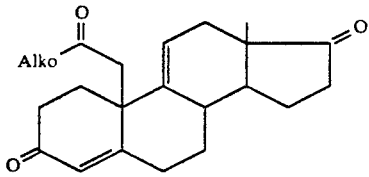
(B)

in which Alk has the meaning above, and reacting the latter to one or two protection reactions of the ketone to obtain a product of formula II.

In a preferred method, the Claisen rearrangement is effected with an alkyl orthoacetate, preferably ethyl, in the presence of an organic acid such as propionic acid and optionally in a solvent such as xylene. The reaction is carried out preferably at high temperature.

The protection reagent of the ketone functions is chosen from alcohols or diols, preferably ethylene glycol. The reaction is carried out preferably in the presence of an acid such as p-toluenesulfonic acid with heating, for example under reflux, in a solvent such as dichloroethane, or using ethylene-glycol itself as the solvent. The product of formula A is described in U.S. Pat. No. 3,282,785.

In addition to the products described in the examples, the following products constitute products being within the scope of the invention in which the substituents R, n, X and Y are those of formula I.

| R | n | X | Y | 1(2) | 6(7) |
|---|---|-----|---|------|------|
| H | O | CH$_2$ | O | ⌐⌐ | ⌐⌐ |
| ClCH$_2$— | O | O | O | ⌐⌐ | ⌐⌐ |

By the expression "12-crown-4" is meant 1, 4, 7, 10 tetraoxacyclododecane; "15-crown-5" represents 1, 4, 7, 10, 13 pentaoxacyclopentadecane; "18-crown-6" represents 1, 4, 7, 10, 13, 16 hexaoxacyclooctadecane.

In the following examples there are described several preferred embodiments to illustrate the invention. However, it should be understood that the invention is not intended to be limited to the specific embodiments.

EXAMPLE 1

10$\beta$-[2-(methylthio)-ethyl]-$\Delta^{4,9(11)}$-estradiene-3,17-dione

STEP A:

3,17-bis(ethylenedioxy)-10$\beta$-(2-hydroxyethyl)-$\Delta^{5,9(11)}$-estradiene A suspension of 380 mg of lithium aluminium hydride in 200 ml of anhydrous tetrahydrofuran was cooled to $-78°$ C. and 4.42 g of ethyl 3,17-bis(ethylenedioxy)-$\Delta^{5,9(11)}$-androstadiene-19-carboxylate dissolved in 50 ml of anhydrous tetrahydrofuran were added. The mixture stood for 30 minutes at "78° C., then for one hour at ambient temperature. The excess hydride was destroyed by the dropwise addition of approximately 10 ml of ethyl acetate. Approximately 50 ml of 2M sodium hydroxide were added and the mixture was extracted with two lots of 150 ml of ethyl acetate, then with one lot of 200 ml of dichloromethane. The organic extracts were dried and concentrated to dryness to obtain 3.98 g of crude product used as is in the following reaction.

NMR (300 MHz CDCl$_3$ + a drop of C$_5$D$_5$N)

0.83 (s, 18 Me); 3.55 to 4.00 (m, —OCH$_2$Ch$_2$— and CH$_2$OH); 5.53 (m, H6 and H 11); 2.33 (S, OH); 1.30 to 2.70 (m, other protons).

STEP B: 3,17-bis(ethylenedioxy)-10$\beta$-[2-(methylsulfonyloxy)-ethyl]-$\Delta^{5,9(11)}$-estradiene A solution of 5.8 g of the product of Step A and 2.21 ml of triethylamine in 70 ml of dichloromethane was cooled to 0° C. and 1.23 ml of mesyl chloride were added dropwise. Then the mixture was stirred for 45 minutes at 0° C. and then was poured into 100 ml of a saturated solution of ammonium chloride. The aqueous phase was extracted with dichloromethane and the combined organic extracts were dried over magnesium sulfate and concentrated to dryness to obtain 6 g of crude mesylate used as is in the following step.

NMR (300 MHz CDCL$_3$ + a drop of C$_5$D$_5$N)

0.83 (s, 18 Me); 2.97 (s, SO$_2$Me); 3.85 to 4.3 (m, ketals and CH$_2$SO$_2$); 5.57 (m) and 5.60 (m) (H6 and H11); 1.2 to 2.6 (m, the other protons).

IR (CHCl$_3$): 1338 and 1175 cm$^{-1}$ (SO$_2$Me)

STEP C:

10$\beta$-[2-(methylthio)-ethyl]-$\Delta^{4,9(11)}$-estradiene-3,17-dione

A mixture of 5.8 g of the mesylate of Step B, 1.81 g of sodium thiomethoxide and 0.26 ml of crown ether (15-crown-5)in solution in 50 ml of anhydrous dimethylformamide was stirred for 12 hours at ambient temperature and was then poured into approximately 50 ml of a saturated solution of ammonium chloride. The aqueous phase was extracted with dichloromethane and the combined organic extracts were dried over magnesium sulfate and concentrated to obtain a crude product which was as is in the following step.

The crude mixture, 20 ml of aqueous 6N hydrochloric acid and 200 ml of 99% ethanol was stirred for one hour at ambient temperature and the mixture was poured into water. The organic phase was extracted with dichloromethane and the combined organic extracts were washed successively with a solution of 1N hydrochloric acid, a saturated solution of potassium bicarbonate and a saturated solution of sodium chloride. After drying and concentrating, the crude mixture was chromatographed on silica with an eluant mixture of ethyl acetate and cyclohexane (3-7), then (1-1) to obtain 3.1 g of the expected product with a Rf=0.45 ethyl acetate - cyclohexane (1-1) which was crystallized from diethyl ether.

NMR (CDCl$_3$, 300 MHz): 0.88 (s, 18 me); 2.10 (s, SMe); 5.55 (m, H11); 5.81 (s, H4).

IR (CHCl$_3$): 1735 cm$^{-1}$ (17-keto), 1665 cm$^{-1}$, 1613 (enone), 1633 cm$^{-1}$ (C=C 9,11)

Analysis: $C_{21}H_{28}O_2S$; molecular weight=344.52
Calculated: %C 73.21; %H 8.19; %S 9.3
Found: 73.0; 8.3; 9.2

Preparation 1:
Ethyl 3,17-bis(ethylenedioxy)-$\Delta^{5,9(11)}$-androstadiene-19-carboxylate Step 1: Ethyl 3,17-dioxo-$\Delta^{4,9(11)}$-androstadiene-19-carboxylate A mixture of 500 mg of $\Delta^{4,9}$-androstadiene-11β-ol-3,17-dione (described in U.S. Pat. No. 3,282,785), 5 ml of triethyl orthoacetate and 6.4 mg of propionic acid was heated to 137° C. and after 4 hours of heating, the reaction mixture was concentrated to dryness. The crude mixture was chromatographed on silica with an eluant mixture of ethyl acetate and hexane (1-1) to obtain 503 mg of the expected product with a Rf=0.33.

NMR (CDCl$_3$, 250 MHz) : 0.94 (s, 18 Me); 1.23 (t, COOCH$_2$CH$_3$) 3.94 to 4.29 (m, COOCH$_2$CH$_3$), 5.61 (m, H11), 5.84 (wide s, H4).

IR (CHCl$_3$) : 1732 cm$^{-1}$ (17-ketone), 1662, 1612 (conjugated ketone).

STEP 2: Ethyl 3,17-bis(ethylenedioxy)-$\Delta^{5,9(11)}$-androstadiene-19-carboxylate 2 ml of ethyleneglycol and 100 mg of p-toluene sulfonic acid were added to a mixture of 503 mg of the product of Step 1 in solution in 30 ml of dichloroethane and the mixture was refluxed for 8 hours. 1 ml of triethylamine was added and the mixture was concentrated, then chromatographed on silica (eluant : ethyl acetate - hexane (3-7) to obtain 450 mg of the expected product with a Rf=0.47 (ethyl acetate - hexane (1-1).

EXAMPLE 2

10β-[2-ethylthio)-ethyl]-$\Delta^{4,9(11)}$-estradiene-3,17-dione

A mixture of 1 g of the mesylate of Step B of Example 1, 0.374 g of sodium thioethoxide and 0.044 ml of crown ether (15-crown-5) in solution in 20 ml of anhydrous dimethylformamide was stirred for 12 hours at ambient temperature and then was poured into approximately 50 ml of a saturated solution of ammonium chloride. The aqueous phase was extracted with dichloromethane and the combined organic extracts were dried over magnesium sulfate. After concentrating, a crude product was obtained which was used as is in the following step.

The crude mixture, 2 ml of aqueous 6N hydrochloric acid and 20 ml of 99% ethanol were stirred for one hour at ambient temperature and was then poured into water. The organic phase was extracted with dichloromethane and the combined organic extracts were washed successively with a solution of 1N hydrochloric acid, a saturated solution of sodium bicarbonate and a saturated solution of sodium chloride. After drying and concentrating to dryness, the crude mixture was chromatographed on silica with an eluant mixture of ethyl acetate and cyclohexane (3-7), followed by (1-1) to obtain 430 mg of the expected product with a Rf=0.45, ethyl acetate - cyclohexane (1-1).

NMR (CDCl$_3$300 MHz): 0.8 (s, 18 me); 1.24 (t, −SCH$_2$−CH$_3$) 5.55 (m, H11); 5.81 (s, H4).

IR (CHCl$_3$): 1735 cm$^{-1}$ (17-keto), 1665 cm$^{-1}$, (enone), 1633 cm$^{-1}$ (C=C 9,11).

Analysis: $C_{22}H_{30}O_2S$; molecular weight=358.55
Calculated: %C 73.70; %H 8.43; %S 8.94
Found: 73.8; 8.5; 9.0

EXAMPLE 3

10β-[2-(acetylthio)-ethyl]-$\Delta^{4,9(11)}$-estradiene-3,17-dione

STEP A:
3,17-bis(ethylenedioxy)-10β-[2-(acetylthio)-ethyl]-$\Delta^{5,9(11)}$-estradiene and
17-(ethylenedioxy)-10β-[2-(acetylthio)-ethyl]-$\Delta^{5,9(11)}$-estradien-3-one A mixture of 3.38 g of the product of Step B of Example 1, 2.3 g of potassium thioacetate and 190 mg of crown ether (18-crown-6) in 60 ml of anhydrous tetrahydrofuran was refluxed and after 15 hours of reflux, the mixture was poured into approximately 100 ml of a saturated solution of ammonium chloride. The combined organic extracts were dried over magnesium sulfate and concentrated under reduced pressure. The residue was chromatographed on silica with an eluant mixture of ethyl acetate and cyclohexane (2-8) to obtain a first fraction of 940 mg consisting of diprotected product I Rf=0.74, ethyl acetate - cyclohexane (1-1). The following fraction constituted 500 mg of the monoprotected product II in position 17 with a Rf=0.44.

Analysis of the diprotected product (I)

NMR (CDCl$_3$, 400 MHz) : 0.86 (s, 18 Me); 2.30 (s, SAc); 3.80 to 4.08 (the ketals), 5.54 (H6and H11).

IR (CHCl$_3$: 1685 cm$^{-1}$ (SC=0).

Analysis of the monoprotected product (II)

NMR (CDCl$_3$, 400 MHz): 0.88 (s, 18 me); 2.31 (s, SAc); .380 to 4.0 (the ketals); 5.56 (H11), 5.77 (H4).

IR (CHCl$_3$): 1683 cm$^{-1}$ (SC=0); 1665 cm$^{-1}$ (enone), 1614 cm$^{-1}$ (C=C).

STEP B:
10β-[2-(acetylthio)-ethyl-$\Delta^{4,9(11)}$-estradiene-3,17-dione

A mixture of 0.5 g of monoprotected product II, 2 ml of aqueous 6N hydrochloric acid and 12 ml of 99% ethanol was added together over one hour at ambient temperature and the mixture was poured into approximately 50 ml of a saturated solution of ammonium chloride. The aqueous phase was extracted with dichloromethane and the combined organic extracts were dried over magnesium sulfate and chromatographed on silica with an eluant mixture of ethyl acetate and cyclohexane (1-1) to obtain 340 mg of the expected product with a Rf=0.3, ethyl acetate - cyclohexane (1-1) which was treated with activated charcoal in dichloromethane, then crystallized from ethyl acetate.

NMR (CDCl$_3$, 300 MHz): 0.96 (s, 18 Me); 2.33 (s, SAc); 5.59 (m, H11); 5.81 (S, H4); 1.1 to 2.8 (other protons).

IR (CHCl$_3$): 1735 cm$^{-1}$, 1680 cm$^{-1}$ (SC=O), 1667 and 1615 cm$^{-1}$ (enone).

Analysis: C$_2$H$_{28}$O$_3$S, S; molecular weight=372.53
Calculated: %C 70.92; %H 7.57; %S 8.60
Found: 71.2; 7.6; 8.9

3,17-bis(ethylenedioxy)-10β(2-(acetylthio)-ethyl)-Δ$^{5,9(11)}$-estradiene of Step A can also be obtained as follows:

1.65 ml of thioacetic acid were added to a mixture of 8.6 g of the product of Example 1 Step A, 10.8 g of triphenylphosphine and 2.6 ml of diethylenedicarboxylate in solution in 100 ml of anhydrous tetrahydrofuran and the mixture was stirred for 2 hours 30 minutes. 0.9 ml of diethyl azodicarboxylate and 0.42 ml of thioacetic acid were added and after 20 minutes of stirring, the solvent was evaporated off. The crude product was chromatographed (eluant : cyclohexane - ethyl acetate (8-2) to obtain 5.99 g of the product identical to that of Step A.

EXAMPLE 4

10β-[2-(methylsulfinyl)-ethyl]-Δ$^{4,9(11)}$-estradiene-3,17-dione

A mixture of 500 ml of the product of Example 1 in 3.7 ml of methanol and 373 mg of sodium periodate solubilized in 3.7 ml of water was stirred for 30 minutes at ambient temperature. The mixture was extracted with methylene chloride and the extracts were dried over magnesium sulfate and brought to dryness. The product was chromatographed on silica (eluant : ethyl acetate - methanol 7-3) to obtain 276 mg of the expected product, 50-50 diasteroisomers.

NMR (CDCl$_3$, 300 MHz): 0.86 and 0.92 (18 Me); 2.56 and 2.58 (S-CH$_3$); 5.59 (m, H11); 5.86 (S, H4).

IR (CHCl$_3$): 1736 cm$^{-1}$ (17-keto), 1668 cm$^{-1}$ (conjugated ketone) 1630 cm$^{-1}$, 1615 cm$^{-1}$ (C=C), 1046 cm$^{-1}$ (S→O).

EXAMPLE 5

10β-[2-(methylsulfonyl)-ethyl]-Δ$^{4,9(11)}$-estradiene-3,17-dione

A mixture of 500 mg of the product of Example 1 in 10 ml of methylene chloride and 600 mg of 80% m-chloroperbenzoic acid was stirred for one hour at 20°) C. and then was neutralized by the addition of a saturated solution of sodium bicarbonate and extracted with methylene chloride. The extracts were dried over magnesium sulfate then brought to dryness under reduced pressure. Purification was carried out by chromatography on silica (eluant : ethyl acetate - methanol (7-3) then with pure ethyl acetate to obtain 450 mg of the sought product with a Rf=0.36, pure ethyl acetate.

NMR (CDCl$_3$, 300 MHz); 0.89 (s, 18 Me); 2.93 (s, SO$_2$Me); 5.59 (m, H11); 5.87 (S, H4); 1.1 to 3.0 the other protons.

IR (CHCl$_3$): 1737 cm$^{-1}$ (17-keto), 1670 cm$^{-1}$ (conjugated ketone) 1632 cm$^{-1}$, 1614 cm$^{-1}$ (C=C), 1319, 1142 cm$^{-1}$ (SO$_2$).

EXAMPLE 6

10β-[[2-(difluoromethyl)-thio]-ethyl]-Δ$^{4,9(11)}$-estradiene-3,17-dione

STEP A:
3,17-bis(ethylenedioxy)-10β-(2-mercaptoethyl)-Δ$^{5,9(11)}$-estradiene 2.3 ml of 64% hydrazine were added at −20° C. to a solution of 3 g of 3,17-bis(ethylenedioxy)-10β-[2-(acetylthio)-ethyl]-$^{5,9(11)}$-estradiene (diprotected product I of Example 3, Step A) in 150 ml of tetrahydrofuran and the mixture stood at −30° C. for 72 hours. The reaction medium was poured into water and extracted with methylene chloride. The extracts were dried over magnesium sulfate and the methylene chloride was evaporated off to obtain 2.65 g of the expected product with a Rf=0.36 (cyclohexane - ethyl acetate (1-1) which was used as is for the following step.

NMR (CDCl$_3$, 300 MHz): 0.82 (s, 18 Me); 3.8 to 4.0 (ketals); 5.49 and 5.53 (m, H6 and H11).

IR (CHCl$_3$); 1635 cm$^{-1}$ and 1672 cm$^{-1}$ (C=C).

STEP B:
3,17-bis(ethylenedioxy)-10β[2-(difluoromethylthio)-ethyl]-Δ$^{5,9(11)}$-estradiene 1 g of the product of Step A in solution in 20 ml of anhydrous tetrahydrofuran was cooled to 20° C. and 322 mg of potassium tertbutoxide were added all at once. The mixture was stirred for 30 minutes at this temperature and a rapid current of freon 22 (ClCHF$_2$) was passed through. The reaction mixture was poured into approximately 100 ml of a saturated solution of ammonium chloride and the organic phase was extracted with dichloromethane. The combined organic extracts were dried over magnesium sulfate and concentrated. After chromatography on silica (eluant : ethyl acetate - cyclohexane (2-8), 500 mg of the expected product were obtained.

NMR (CDCl$_3$, 300 MHz): 0.82 (s, 18 Me); 3.86 to 4.0 (the ketals), 5.54 (the ethylenics), 6.76 (t, SCHF$_2$, J=56.5 Hz).

IR (CHCl$_3$): weak absorptions (C=C) 1615 and 1638 cm$^{-1}$, probable C—O—C.

STEP C:
10β-[[2-(difluoromethyl)-thio]-ethyl]-Δ$^{4,9(11)}$-estradiene-3,17-dione A mixture of 90 mg of the product of Step B, 1 ml of aqueous 3N hydrochloric acid and 5 ml of 99% ethanol was stirred for 10 minutes at 0° C. and then for 30 minutes at ambient temperature. The mixture was poured into a saturated solution of sodium bicarbonate and the organic phase was extracted with dichloromethane. The combined organic extracts were dried over magnesium sulfate and concentrated under reduced pressure to obtain 61.7 mg of crude product which was chromatographed on silica with an eluant mixture of ethyl acetate and cyclohexane (1-1 to obtain 46.5 mg of the expected product.

NMR (CDCl$_3$, 300 MHz): 0.88 (s, 18 Me); 5.82 (s, H4); .68 (t, CHF$_2$, J=55.5 Hz).

IR (CHCl$_3$): 1736 cm$^{-1}$, (17-keto); 1666 and 1614 and 867 cm$^{-1}$ (enone); strong absorptions 1060, 1030 cm$^{-1}$ (CHF$_2$).

EXAMPLE 7

10β-[2-(methylthio)-ethyl]-Δ$^{1,4,9(11)}$-estratriene-3,17-dione

A mixture of 500 mg of the product of Example 1, 830 mg of dichlorodicyanoquinone and 20 ml of dioxane was refluxed for one hour and then stirred overnight at ambient temperature. The mixture was concentrated and chromatographed on silica with an eluant mixture of ethyl acetate and cyclohexane (3-7), followed by (1-1) to obtain the expected product with a Rf=0.43, ethyl acetate - cyclohexane - (1-1, which was chromatographed again with an eluant mixture of ethyl acetate and cyclohexane (2-8) to obtain 280 mg of the pure product.

NMR (CDCl$_3$, 300 MHz): 0.95 (s, 18 Me); 2.07 (s, SMe); 5.62 (m, H11); 6.19 (s, H4); 6.39 (dd, H2); 7.10 (d, H1).

IR (CHCl$_3$): 1736 cm$^{-1}$, (17-keto); 1664 cm$^{-1}$, 1625 cm$^{-1}$, 1607 cm$^{-1}$, 891 cm$^{-1}$ (delta 1,4 3-one).

EXAMPLE 8

10β-[2-(methylthio)-ethyl]-$^{4,6,9(11)}$-estratriene-3,17-dione

A mixture of 1.15 g of the product of Example 1, 4.17 ml of ethyl orthoformate and 30 mg of p-toluene sulfonic acid was stirred for 90 minutes at ambient temperature. Then, 5 ml of triethylamine were added and the mixture was poured into approximately 150 ml of a saturated solution of sodium bicarbonate. After extraction with methylene chloride, the combined organic phases were dried over magnesium sulfate and 2 ml of triethylamine were added and then the solvent was evaporated. The 1.2 g of product was mixed with 1.5 g of chloranile in 56 ml of an acetone - water mixture (95-5) and after stirring 90 minutes at ambient temperature, the medium was poured into 150 ml of a saturated solution of sodium thiosulfate. 150 ml of a saturated solution of sodium bicarbonate were added and after further stirring for 90 minutes at ambient temperature, the aqueous phase was extracted with methylene chloride, then with ethyl acetate. The organic extracts were dried over magnesium sulfate and then evaporated to dryness. The crude product was chromatographed under pressure to obtain 920 mg of the expected product.

NMR (CDCl$_3$, 300 MHz): 0.96 (s, 18 Me); 2.10 (s, SMe); 2.92 (wide d, H8); 5.59 (n, H11); 5.76 (s, H4); 6.22 (AB, H6 and H7).

IR (CHCl$_3$): 1739 cm$^{-1}$, (17-keto); 1659 cm$^{-1}$, 1624 cm$^{-1}$, 1583 cm$^{-1}$, 877 cm$^{-1}$ (delta 4,6 3-one).

Analysis: C$_{21}$H$_{26}$O$_2$S; molecular weight=342.5
Calculated: %C 73.64; %H 7.65; %S 9.36
Found: 73.5; 7.7; 9.2

EXAMPLE 9

10β-[2-(methylthio)-ethyl]-3-methylene-Δ$^{4,9(11)}$-estradien-17-one

A mixture of 2.07 g of triphenyl methylphosphonium bromide in 10 ml of ether and 3.75 ml of butyl lithium was stirred for 20 minutes at ambient temperature and 0.5 g of the product of Example 1 in solution in 10 ml of ether were added. The reaction medium was stirred for 30 minutes at ambient temperature and poured into 30 ml of water. After extraction with ethyl acetate, the combined organic extracts were dried over magnesium sulfate, and the solvent was evaporated. The residue was purified by chromatography under pressure to obtain 190 mg of the expected product with a Rf=0.37 cyclohexane - ethyl acetate (8-2).

NMR (CDCl$_3$, 300 MHz): 0.86 (s, 18 Me); 2.08 (s, SMe); 4.68 (s) and 4.73 (s) (CH$^2$=C); 5.47 (n, H11); 5.9 (s, H4).

EXAMPLE 10

10β-[2-(acetythio)-ethyl]-3-methylene-Δ$^{4,9,(11)}$-estradien-17-one 0.34 ml of n-butyl lithium were added dropwise with stirring to a suspension of 195.6 mg of triphenyl methyl phosphonium bromide in 10 ml of anhydrous ethyl ether and then the mixture was stirred for 20 minutes at ambient temperature. A solution of 51 mg of the product of Example 3 in 5 ml of anhydrous ether was introduced slowly and the mixture was stirred for 12 hours at ambient temperature, then for one hour under ether reflux. The crude mixture was poured into approximately 30 ml of ice-cooled water and the aqueous phase was extracted with ethyl acetate. The combined organic extracts were concentrated and chromatography on silica with an eluant mixture of ethyl acetate and cyclohexane (2-8) yielded 7.3 mg of the expected product with a Rf=0.6.

Analysis

NMR (CDCl$_3$, 300 MHz): 0.93 (s, 18 Me); 2.31 (s, CH3—C=); 4.68 and 4.72 (CH$_2$—C): 5.51 (m, H11); 5.89 (H4).

EXAMPLE 11

10β-[2-(methyldithio)-ethyl]-Δ$^{4,9(11)}$-estradiene-3,17-dione

STEP A:

3,17-bis(ethylenedioxy)-10β-[2-(methyldithio)-ethyl]-Δ$^{5,9(11)}$-estradiene

A mixture of 202 mg of potassium tert-butylate in 0.17 ml of methyl methane-thio-sulfonate was added at −71° C. to a mixture of 750 mg of 3,17-bis(ethylenedioxy)-10β-(2-mercapto ethyl)-$^{5,9(11)}$-estradiene in approximately 50 ml of tetrahydrofuran. The mixture was stirred while allowing the temperature to return to ambient temperature over 2 hours, then at −30° C. for 48 hours. 20 ml of an aqueous solution of ammonium chloride were added, followed by extraction with methylene chloride. The organic extracts were dried over magnesium sulfate and the solvent was evaporated to obtain 372.6 mg of the expected product with a Rf=0.14 (same eluant as above).

NMR (CDCl$_3$, 400 MHz) 0.85 (s, 18 Me); 2.36 (s, CH$_3$—S—); 3.82 to 4 (ketals); 5.5 and 5.53 (H6 and H11); 2.52 (t, S—CH$_2$—CH$_2$).

STEP B:

10β-[2-(methyldithio)-ethyl]-Δ$^{4,9(11)}$-estradiene-3,17-dione

A mixture of 100 mg of the product of Step A in 4 ml of ethanol and 1.2 ml of 6N hydrochloric acid was stirred for one hour at ambient temperature and 5 ml of a saturated solution of sodium bicarbonate were added, followed by extraction with methylene chloride. The combined organic extracts were dried over magnesium sulfate and the solvent was evaporated. The residue was chromatographed (eluant : cyclohexane - ethyl acetate (1-1)) to obtain 35 mg of the expected product as a yellow oil with a Rf=0.6 (same eluant as above).

NMR (CDCl$_3$, 300 MHz): 0.90 (18 Me); 2.38 (S—S Me); 5.54 (H11); 5.82 (H4).

IR (CHCl$_3$): 1735 cm$^{-1}$, (17-keto); 1655 cm$^{-1}$ (conjugated ketone); 1663-1614 (C=C).

EXAMPLE 12

10β-[2-(thiocyanato)-ethyl]-Δ$^{4,9(11)}$-estradien-3,17-dione

Using the procedure of Example 11, the expected product was prepared.

IR (CHCl$_3$): 1736 cm$^{-1}$ (17-keto); 1671 cm$^{-1}$ (conjugated ketone), 1633 and 1616 cm$^{-1}$ (C=C), 2158 cm$^{-1}$ (S—C≡N).

NMR (CDCl$_3$, 250 MHz): 0.88 (s, 18 Me); 5.57 (m, H11); 5.85 (d, H$_4$)

EXAMPLE 13

10β-[2-(methylthio)-ethyl]-Δ$^{4,9(11)}$-estradien-17-ol-3-one

A solution of 2.38 g of 10β2 -[2-(methylthio)-ethyl-Δ$^{4,9(11)}$-estradien-3,17-dione of Example 1 and 600 ml of a methanol-dichloromethane mixture (1-1) was cooled to −78° C. and 2.34 g of sodium borohydride were added followed with stirring for 6 hours at −78° C. 150 ml of acetone were added and the mixture was allowed to return to ambient temperature, partially concentrated and the treatment with sodium borohydride was repeated with further stirring for 6 hours. After having added another 150 ml of acetone, concentration was carried out under reduced pressure, followed by acidification using 2N hydrochloric acid and extraction with dichloromethane. The organic phases were dried, concentrated and chromatographed on silica (eluant : ethyl acetate - cyclohexane 3-7) to obtain 229 mg of the expected product.

NMR (300MHz CDCl$_3$): 0.75 (s, 18 Me); 2.11 (s, S—Me); 5.53 (m, H11); 5.79 (d, H4); 8 to 2.7 (m, the protons)

IR (CHCl$_3$): 3615 cm$^{-1}$ (OH), 1665 and 1612 cm$^{-1}$ (enone).

EXAMPLE 14

10β-[2-[(2-hydroxyethyl)-thio]-ethyl]-Δ$^{4,9(11)}$-estradien-3,17-dione

STEP A:

3,17-bis-(ethylenedioxy)-10β-[2-hydroxyethyl)-thio]-ethyl]-Δ$^{5,9(11)}$-estradiene 6.7 g of potassium tert-butylate were added at ambient temperature to a mixture of 4.2 ml of 2-mercapto ethanol and 150 ml of dimethylformamide and the mixture was stirred for one hour, 4 g of 3,17-bis-(ethylenedioxy)-10β-[2-(acetylthio)-ethyl]-Δ$^{5,9(11)}$-estradiene obtained as in Example 1, Step B)in 50 ml of dimethylformamide were added and the solution was stirred for 2 hours. The dimethylformamide was eliminated under reduced pressure, and the reaction mixture was poured into an ethyl acetate - water mixture (3-1). The organic phase was decanted, dried, and the solvents were eliminated under reduced pressure to obtain 2.4 g of the expected product.

NMR (CDCl$_3$, 250 MHz): 0.82 (s, 18 Me); 3.8 to 4 (the ketals); 5.52 (the ethylenics), 2.70 (t) 2H and 3.68 (t) 2H (S—CH$_2$—CH$_2$).

STEP B:

10β-[2-[(2-hydroxyethyl)-thio]-ethyl]-Δ$^{4,9(11)}$-estradien-3,17-dione 1 g of the product of Step A in 50 ml of methanol and 5 ml of 6N hydrochloric acid were stirred for one hour at ambient temperature and the solvents were evaporated off. The residue was taken up in a mixture of water, sodium bicarbonate and ethyl acetate and after decanting, the organic phase was dried. After chromatography on silica (eluant : cyclohexane - ethyl acetate 40-60 ), 0.8 g of the expected product were obtained.

IR:3618 cm$^{-1}$ (OH): 1736, 1665 cm$^{-1}$ (ketone and conjugated ketone); 1634 and 1613 cm$^{-1}$ (ethylenic)

NMR (CDCl$_3$, 300 MHz): 0.81 (s, 18 Me); 5,49 and 5.75 (ethylenics); 2.65 (t) 2H and 3.66 (t) 2H (—SCH$_2$CH$_2$).

EXAMPLE 15

10β[2-[(2-chloroethyl)-thio]-ethyl]-Δ$^{4,9(11)}$-estradien-3,17-dione 553 mg of the product of Example 14 are stirred for 2 hours at ambient temperature with 0.13 ml of mesyl chloride and 0.23 ml of triethylamine in 50 ml of methylene chloride and the reaction mixture was washed with water. The organic phase was separated and dried and the solvent was evaporated off. The residue was chromatographed on silica (eluant : cyclohexane -ethyl acetate 7-3) to obtain 160 mg of the expected product.

IR 1634, 1614 cm$^{-1}$ (ethylenic); 1736, 1666 cm$^{-1}$ (carbonyl),

NMR (CDCl$_3$, 300 MHz): 0.88 (s, 18 Me); 5.56 (m), 5.82 (d) ethylenic; 2.85 (dd) 2H and 3.61 (t) 2H (—S—CH$_2$CH$_2$).

EXAMPLE 16

10β-[2-[(2-dinitrophenyl)-dithio]-ethyl]-Δ$^{4,9(11)}$-estradien-3,17-dione

STEP A:

3,17-bis-(ethylenedioxy)-10β-[2-[(2,4-dinitrophenyl)-dithio]-ethyl]-Δ$^{4,9(11)}$-estradien 416 mg of 3,17-bis-(ethylenedioxy)-10β-[2,-difluoromethylthio)-ethyl]-Δ$^{5,9}$(11)-estradiene and 81 microliters of pyridine in 15 ml of methylene chloride were mixed together under an inert atmosphere and then 235 mg of 2,4-dinitrobenzene sulfenyl chloride in solution in 5 ml of methylene chloride were added. After stirring for 30 minutes, the reaction mixture was poured into 100 ml of water and 100 ml of ethyl acetate. The organic phase was separated and dried and the solvent was evaporated under reduced pressure. The residue was chromatographed on silica (eluant : cyclohexane - methylene chloride - ethyl acetate) to obtain 500 mg of expected product.

IR 1594, 1526 cm$^{-1}$ (F) (aromatic and nitro)

NMR (CDCl$_3$, 300 MHz): 0.6 (s, 18 Me); 5.46 (d), 5.53 (d) (the ethylenics); 3.8 to 4 (the ketals); 8.47 (s) 2H and 9.11 (s) 1H (phenyl).

STEP B:

10β-[2-[(2,4-dinitrophenyl)-dithio]-ethyl]-Δ$^{4,9(11)}$-estradien-3,17-dione 1.25 g of the product of Step A and 10 ml of 6N hydrochloric acid in 150 ml of methanol were mixed together under an inert atmosphere and after dissolution, the solvents were evaporated. The residue was taken up in a water - sodium bicarbonate - ethyl acetate mixture and the organic phase was decanted and dried. The solvents were eliminated under reduced pressure and the residue was chromatographed on silica (eluant : methylene chloride - ether 100-0 then 90-10) to obtain 1 g of the expected product.

IR 1595, (S) 1528 cm$^{-1}$ (F) (aromatic and nitro); 1737 and 1668 cm$^{-1}$ (carbonyl); 1638 and 1613 cm$^{-1}$ (ethylenics).

NMR (CDCl$_3$, 300 MHz): 0.63 (s, 18 Me); 5.51 (m), 5.82 (s) (ethylenics); 8.48 (s) 2H and 9.10 (s) 2H (phenyl); 1.1 to 2.8 (other protons).

EXAMPLE 17

10β-[2-(ethenylthio)-ethyl]-Δ$^{4,9(11)}$-estradien-3,17-dione 265 mg of the product of Example 16 in 50 ml of tetrahydrofuran were cooled to −78° C. under an inert atmosphere and then 1 ml of vinyl magnesium bromide was added slowly. The mixture was stirred for one hour at −κ° C., then allowed to return to ambient temperature. After stirring for 30 minutes, a saturated aqueous solution of ammonium chloride was added and the tetrahydrofuran was eliminated under reduced pressure. Extraction was carried out with ethyl acetate and the organic phase was separated and dried. The solvent was eliminated under reduced pressure and the residue was crystallized from isopropyl ether to obtain 40 mg of expected product.

IR 1736 cm$^{-1}$ (carbonyl); 1736 cm$^{-1}$ (delta 4-3-one); 1585 and 956 cm$^{-1}$ (thiovinyl).

NMR (CDCl$_3$, 300 MHz): 0.88 (s, 18 Me); 5.59 (m) and 5.82 (d) (the ethylenics); 5.12 (d-16.5 Hz); and 5.23 (d, J=10 ) (CH$_2$—CH—S); 6.29 (dd J=10 and 16.5) (S—CH—CH$_2$); 1.1 to 2.7 (the other protons).

EXAMPLE 18

10β-[2-(methylthio)-ethyl]-Δ$^{4,9(11)}$-estradien-3,17-dione dioxime 200 mg of the product of Step C of Example 1 in 10 ml of methylene chloride and 40 mg of ammonium chloride in the presence of a little magnesium sulfate were mixed together at ambient temperature. 0.08 ml of triethylamine was added dropwise followed by stirring for 30 minutes, and heating at reflux for one hour and half. The mixture was stirred at ambient temperature for 48 hours and then was filtered through celite and purified by chromatography (eluant: cyclohexane-ethyl acetate 8-2) to obtain 145 mg of crude product which was crystallized from ether to obtain 46.5 mg of the expected product.

IR (CHCl$_3$): 3885 cm$^{-1}$ (OH, oxime); 1635 cm$^{-1}$ (C=C); 1620 cm$^{-1}$ (C≡N).

NMR (CDCl$_3$, 300 MHz): 0.91 (s, 18 Me); 2.08 (s, SME); 5.50 (m, H11); 5.86 (s, H4 (E)); 7.54 and 7.78 (the OH's).

EXAMPLE 19

10β-[2-(phenylthio)-ethyl]-Δ$^{4,9(11)}$-estradien-3,17-dione

STEP A:
3,17-bis-(ethylenedioxy)-10β-[2-(phenylthio)-ethyl]-Δ$^{4,9(11)}$-estradiene Sodium thiophenyloxide was prepared by mixing at ambient temperature 0.510 md of sodium in 40 ml of tetrahydrofuran and 5.6 ml of thiophenol. After 12 hours of stirring, the precipitate was filtered and washed with pentane, then dried under reduced pressure. 300 mg of mesylate prepared in Step B of Example 1 were mixed with 20 ml of dimethylformamide and 165 mg of sodium thiophenyloxide were added. The mixture was stirred for 24 hours at ambient temperature and the 5 drops of 15-crown 5 ether were added, followed by stirring for 12 hours. The solvent was eliminated under reduced pressure and after chromatography on silica (eluant: hexane-acetate 8-2), 281 mg of the expected product were obtained.

IR (CHCl$_3$): 1584, 1481 cm$^{-1}$ (S—C$_6$H$_5$).

NMR (CDCl$_3$, 300 MHz): 0.80 (s, 18 Me); 3.85 to 3.98 (ketals); 5.57 (m, H6 and H11); 7.14 to 7.33 (S—C$_6$H$_5$); 1.25 to 2.90 (other protons).

STEP B:
10β-[2-(phenylthio)-ethyl]-Δ$^{4,9(11)}$-estradien-3,17-dione

A mixture of 260 mg of the product of Step A in 20 ml of ethanol and 2 ml of 6N hydrochloric acid was stirred for one hour at ambient temperature. Hydrolysis was carried out with a saturated solution of sodium bicarbonate, followed by extraction with methylene chloride. The combined organic extracts were dried over magnesium sulfate and the solvent was evaporated off. The residue was chromatographed (eluant: cyclohexane-ethyl acetate 8-2) to obtain 121 mg of the expected product which was crystallized from ether for a Rf=0.55 (eluant: cyclohexane-ethyl acetate 1-1).

NMR (CDCl$_3$, 300 MHz): 0.84 (18 Me); 2.38 (S—S Me); 5.57 (H11); 5.78 (H4); 7.20 to 7.40 (phenyl).

IR (CHCl$_3$): 1736 cm$^{-1}$ (17-keto); 1665 cm$^{-1}$ (conjugated ketone); 1630, 1612, 1577, 1477 cm$^{-1}$ (C=C+aromatic).

EXAMPLE 20

10β-[2-(2-propenylthio)-ethyl]-Δ$^{4,9(11)}$-estraden-3,17-dione

STEP A:
3,17-bis(ethylenedioxy)-10β-[2-(2-propenylthio)-ethyl]-Δ$^{4,9(11)}$-estradiene Using the procedure of Example 19, Step A, 120 mg of sodium and 0.36 ml of allyl mercaptan, 1 g of the mesylate of Example 1, Step B, 20 ml of dimethylformamide and 0.44 ml of 15-Crown-5 ether were reacted to obtain 282 mg of expected product.

NMR (CDCl$_3$, 300 Mhz): 0.83 (s, 18 Me); 3.11 (m, S—CH$_2$—C=); 3.8 to 4.0 (the ketals); 5.05 to 5.20 (m, CH$_2$=); 5.51 (m, H6 and H11); 5.77 m, CH=).

STEP B:
10β-[2-(2-propenylthio)-ethyl]Δ$^{4,9(11)}$-estradien-3,17-dione

Using the procedure of Step B of Example 19, 300 mg of the product of Step A and 5 ml of 6N hydrochloric acid were reacted to obtain 230 mg of crude product which was crystallized from pentane.

IR (CHCl$_3$): 1736 cm$^{-1}$ (17-keto); 1665 cm$^{-1}$ (conjugated ketone); 1634, 1613 cm$^{-1}$ (C=C); 921 cm$^{-1}$ (CH=CH$_2$).

NMR (CDCl$_3$, 300 MHz): 0.88 (s, 18 Md); 3.13 (dd, J−1 and 7, S—CH$_2$—C=); 5.05 to 5.11 (CH$_2$=CH); 5.54 (m, H11);l 5.73 (m, CH$_2$=CH); 5.81 (H4).

3,17-bis-(ethylenedioxy)-10β-[2-(2-propenylthio)-ethyl]-Δ$^{4,9(11)}$-estradiene of Step A can also be obtained as follows:

400 mg of the product of Step A of Example 6 were dissolved in 10 ml of tetrahydrofuran and 129 mg of potassium tert-butylate were added. The mixture was stirred for 40 minutes at ambient temperature and 0.16 ml of allyl bromide were added followed by stirring for a further 30 minutes. Next, a saturated aqueous solution of ammonium chloride was added and extraction was carried out with methylene chloride. The extracts were dried and the solvent was evaporated off. After chromatography (eluent: cyclohexane-ethyl acetate 8-2), 325 mg of the expected product were obtained.

NMR (CDCl$_3$, 300 MHz): 0.82 (s, 18 Me); 3.11 (d, S—CH$_2$—C≡); 3.8 to 4 (the ketals); 5.0 to 5.15 (CH$_2$=CH); 5.50 (m, H6 and H11); 5.76 (m, CH$_2$=CH).

EXAMPLE 21

10β-2-(ethynylthio)-ethyl-Δ$^{4,9(11)}$-estradien-3,17-dione

STEP A:

10β-[2-(trimethylsilylpropynylthio)-ethyl]-Δ$^{4,9(11)}$-estradien-3,17-dione 0.14 ml of trimethylsilylacetylene in solution in 60 ml of tetrahydrofuran was cooled to −78° C. under an inert atmosphere and 0.91 ml of n-butyllithium were added. The mixture was stirred for 15 minutes, and then at −78° C., it was poured into 528 mg of disulfide (in Step B of Example 15) in solution in 20 ml of tetrahydrofuran cooled to the same temperature. The mixture was stirred for one hour and taken up in a saturated aqueous solution of ammonium chloride. The solvent was eliminated under reduced pressure and extraction was carried out with ethyl acetate. The organic phase was dried and the solvent was evaporated. The residue was chromatographed on silica (eluant: methylene chloride-ether 90-10) to obtain 180 mg of the expected product.

IR 2092 cm$^{-1}$ (acetylenic); 1636 and 1616 cm$^{-1}$ (ethylenic); 1736 and 1666 cm$^{-1}$ (carbonyl).

STEP B:

10β-[2-(ethynylthio)-ethyl]-Δ$^{4,9(11)}$-estradiene-3,17-dione 110 mg of the product of Step A and 0.3 ml of tetrabutylammonium fluoride in 20 ml of tetrahydrofuran were mixed together at ambient temperature under an inert atmosphere. After stirring for 15 minutes, the reaction medium was taken up in water and extracted with ethyl acetate. The organic phase was separated and dried and the solvents were evaporated. After chromatographing the residue on silica (eluant: cyclohexane-ethyl acetate 7-3), 60 mg of the expected product melting at 174° C. were obtained.

IR 3301 cm$^{-1}$ (acetylenic); 1667, 1614 cm$^{-1}$ (enone); 1736 cm$^{-1}$ (ketone).

NMR (CDCl$_3$, 300 MHz): 0.88 (s, 18 Me); 5.57 (t), 5.83 (d) (the dienes); 2.80 (s, the acetylenic).

EXAMPLE 22

10β-[2-fluoromethylthio)-ethyl]-Δ$^{4,9(11)}$-estradien 3,17-dione 482 mg of the product of Example 4 were dissolved in 1.34 ml of chloroform and 12.8 mg of zinc iodide were added drop wise. Then 431 mg of diethylaminosulfide trifluoride were added, and the mixture was stirred for 3 hours at ambient temperature, then heated for one hour at 50° C. After concentrating under reduced pressure, the residue was chromatographed on silica (eluant: ethyl acetate-cyclohexane 3-7) and after crystallization from ether, 144 mg of the expected product were obtained.

IR (CHCl$_3$) 1735 cm$^{-1}$ (17-keto); 1667, 1614 cm$^{-1}$ (enone).

NMR (CDCl$_3$, 300 MHz): 88 (s, 18 Me); 5.58 (m, H11); 5.82 (d, H4); 5.49 (d, JHF=53 Hz, SCH$_2$F).

EXAMPLE 23

10β-[2-(phenyldithio)-ethyl]-Δ$^{4,9(11)}$-estradien-3,17-dione

STEP A:

3,17-bis-(ethylenedioxy)-10β-[2-(phenyldithio)-ethyl]-Δ$^{4,9(11)}$-estradiene 617 mg of the product of Example 16 and 400 mg of sodium thiophenate in 80 ml of tetrahydrofuran were mixed together at ambient temperature under an inert atmosphere and the mixture was stirred for one hour, then taken up in a saturated aqueous solution of ammonium chloride. The tetrahydrofuran was eliminated under reduced pressure, and extraction was carried out with ethyl acetate. The organic phase was concentrated to dryness and the residue was chromatographed on silica (eluant: cyclohexane-ethyl acetate 75-25) to obtain 270 mg of the expected product.

IR 1581, 1477 cm$^{-1}$ (thiophenol).

NMR (CDCl$_3$) 300 MHz 0.7 (s, 18 Me); 3.8 to 4 (the ketals); 5.45, 5.50 the dienes); 7.15 to 7.35 (3H) 7.50 (2H) (phenyl).

STEP B:

10β-[2-(phenyldithio)-ethyl]-Δ$^{4,9(11)}$-dien-3,17-dione

Using the procedure of Step B of Example 19, 270 mg of the product of Step A, 5 ml of 6N hydrochloric acid and 50 ml of methanol were reacted to obtain 105 mg of the expected product.

IR 1630, 1612, 1580 and 1477 cm$^{-1}$ (aromatic and ethylenic); 1736 and 1665 cm$^{-1}$ (carbonyl).

NBR (CDCl$_3$, 300 MHz): 0.69 (s, 18 Me); 5.48 (m); 5.78 (d) (the dienes); 7.23 (m), 7.32 (tm), 7.50 (dm) (the phenyl).

EXAMPLE 24

10β-[2-(cyclopropylthio)-ethyl]-Δ$^{4,9(11)}$-estradien-3,17-dione

STEP A:

3,17-bis-(ethylenedioxy)-10β-[2-(cyclopropylthio)-ethyl]-Δ$^{4,9(11)}$-estradiene Using the procedure of Example 21, 0.36 ml of bromocyclopropane, 0.65 ml of tert-butyllithium, 617 mg of the product of Example 16 and 30 ml of tetrahydrofuran were reacted to obtain after chromatographing the crude product on silica (eluant: cyclohexane-methylene chloride-ether 50-50-5), 170 mg of the expected product.

STEP B:

10β-[2-(cyclopropylthio)-ethyl]-Δ$^{4,9(11)}$-estradien-3,17-dione

Using the procedure of Step B of Example 19, 170 mg of the product of Step A, 3 ml of 6N hydrochloric acid and 30 ml of methanol were reacted to obtain 75 mg of the expected product.

IR 1786 and 1665 cm$^{-1}$ (carbonyl); 1633, 1613 cm$^{-1}$ (ethylenic).

NMR (CDCl$_3$, 300 MHz): 0.90 (s, 18 Me); 5.56 (m), 5.81 (s) (the dienes); 0.53 (m), 0.84 (m) (the cyclopropyl); 1.1 to 2.7 (other protons).

10β-[2-[[(methylthio)-methyl]-thio]-ethyl]-Δ$^{4,9(11)}$-estradien-3,17-dione

STEP A:

3,17-bis-(ethylenedioxy)-10β-[2-[[(methylthio)-methyl]-thio]-ethyl]-Δ$^{4,9(11)}$-estradiene Using the procedure of Step A of Example 20, (second method) 1 g of the product of Example 6, Step A, 322 mg of potassium tert-butylate and 0.4 ml of methyl chloromethylsulfide were reacted to obtain 850 mg of expected product.

IR (CHCl$_3$): 1732 cm$^{-1}$ (17-keto); 1670, 1634 cm$^{-1}$ (C=C).

NMR (CDCl$_3$, 1 drop of C$_5$D$_5$N, 300 MHz): 0.85 (s, 18 Me); 2.13 (s, SMe); 3.62 (s, S—CH$_2$—S); 3.8 to 4 (ketals); 5.53 (m, H6 and H11).

STEP B:

10β-2-[[(methylthio)-methyl]-thio]ethyl]-Δ$^{4,9(11)}$-estradien-3,17-dione

Using the procedure of Step B of Example 19, 350 mg of the product of Step A, 6 ml of 6N hydrochloric acid and 12 ml of ethanol were reacted to obtain 270 mg of the expected product.

IR-(CHCl$_3$): 1736 cm$^{-1}$ (17-keto), 1664, 1613 cm$^{-1}$ (delta-4,3-one). NMR (CDCl$_3$, 250 MHz): 0.91 (s, 18 Me); 2.13 (s, S—CH$_2$—S); 5.58 (m, H11); 5.82 (d, H4).

EXAMPLE 26

10β-[2-(methylthio)-ethyl]-Δ$^{4,9(11)}$ estradien-3β,17β-diol and 3α,17β-diol isomer Using the procedure of Example 17, 1 g of the product of Example 1, Step C, 110 mg of lithium-aluminium hydride in 25 ml of tetrahydrofuran were reacted while stirring for 24 hours. After extraction with methylene chloride, the solvent was eliminated under reduced pressure and the residue was chromatographed (eluant: cyclohexane-ethyl acetate 1-1) to obtain 401 mg of 3β,17β-isomer which was cystallized from ether, and 281 mg of 3α, 17β, isomer.

3α,17β-diol isomer

IR (CHCl$_3$): Absence of ketone; 3611 cm$^{-1}$ strong OH).

NMR (CDCl$_3$): 0.72 (s, 18 Me); 2.09 (s,SMe); 3.73 (t, H17); 4.18 (m, H3); 5.39 (m, H4 and H11).

3α,17β-diol isomer

IR (CHCl$_3$): Absence of ketone; 3608 cm$^{-1}$ (strong OH).

NMR (CDCl$_3$): 0.72 (s, 18 Me); 3.73 (t, H17); 4.11 (m, H3); 5.48 (m, H4 and H11).

EXAMPLE 27

Butanedioate of 10β-[2-(methylthio)-ethyl]-3-oxo-Δ$^{4,9(11)}$-estradien-17β-yl and of sodium 704 mg of the product of Example 13 were dissolved at ambient temperature and under an inert atmosphere in 10 ml of chloroform and 814 mg of succinic acid were added. Then 2.8 ml of triethylamine were added dropwise and finally 198 mg of dimethylaminopyridine were added. After stirring for 12 hours at ambient temperature, 100 ml of 2N hydrochloric acid were added and extraction was carried out with chloroform. The extracts were dried and the solvents were eliminated to obtain 280 mg of residue in the form of the acid which was dissolved in 1 ml of ethanol and 1 ml of water and then 34.5 mg of sodium bicarbonate were added. After stirring for 2 hours at ambient temperature, the solvent was eliminated under reduced pressure. The residue was taken up in 10 ml of water, filtered through celite and lyophilized to obtain 199 mg of the expected product.

IR (CHCl$_3$): 1720 cm$^{-1}$ (17-keto); 1666 cm$^{-1}$ (conjugated ketone); 1611, and 1587 cm$^{-1}$ (C=C and COO).

NMR (CDCl$_3$, 300 MHz): 75 (s, 18 Me); 2.09 (s, SMe); 4.62 (t, H17); 5.46 (H11); 5.79 (H4).

EXAMPLE 28

10β-[2-(methylthio)-ethyl]-16α-methyl-Δ$^{4,9(11)}$-estradien-3,17-dione 1.1 g of the product of Example 1, Step C, were dissolved under an inert atmosphere in 30 ml of tetrahydrofuran and after the solution was cooled to −78° C., 3.52 ml of a 1M solution lithium hexamethyldisilylamide in tetrahydrofuran were added. After stirring for 20 minutes, 0.2 ml of methyl iodide were added and the mixture was allowed to return to ambient temperature. After chromatography on silica (eluant: ethyl acetate-cyclohexane 3-7), 590 mg of the expected product were obtained.

NMR (CDCl$_3$, 300 MHz): 0.91 (s, 18 Me); 1.12 (d, CH$_3$—CH); 2.1 (s, SMe); 5.54 (H11); 5.81 (H4).

EXAMPLE 29

7α-[(4-aminophenyl)-thio]-[2-(methylthio)-ethyl]-Δ$^{4,9(11)}$-estradien-3,17-dione 1.2 g of 4-aminothiophenol and 23 mg of sodium were added to 470 mg of the product of Example 8 in 10 ml of tetrahydrofuran and the mixture was stirred for 12 hours at ambient temperature. The reaction medium was poured into 30 ml of a saturated aqueous solution of ammonium chloride and extracted with methylene chloride. The organic phase was separated and dried, and the solvents were eliminated under reduced pressure. After chromatography on silica (eluant: ethyl acetate-cyclohexane 1-1), 174 mg of the expected product were obtained.

IR (CHCl$_3$): 3500, 3400 cm$^{-1}$ (=C—NH$_2$); 1664 cm$^{-1}$ (enone); 1620, 1598, 1495 cm$^{-1}$ (C=C aromatics NH$_2$ def).

NMR (CDCl$_3$, 300 MHz): 0.88 (s, 18 Me); 2.5 (s, SME); 5.68 (m, H11); 5.77 (s, H4 ); 6.6 to 6.8 and 7.0 to 7.4 (m, aromatics); 3.91, 3.65 and 3.46 (m, H7+other absorption); 0.8 to 3 (m, other protones).

EXAMPLE 30

10β-[2-(methyldithio)-ethyl]-Δ$^{4,9(11)}$-estradien-3,17-dione

STEP A:

3,17-bis-(ethylenedioxy)-10β-[2-(methyldithio)-ethyl]-Δ$^{4,9(11)}$-estradiene

Using the procedure of Step A of Example 23, at 0° C. 625 mg of the product of Example 16 and 300 mg of sodium thiomethoxide in 50 ml of tetrahydrofuran were reacted to obtain 227 mg of the expected product. IR Spectrum identical to that obtained in example 11A.

STEP B:
10β-[2-(methyldithio)-ethyl]-Δ$^{4,9(11)}$-estradien-3,17-dione

Using the procedure of Step B of Example 19, 100 mg of the product of Step A in 4 ml of ethanol and 1.2 ml of 6N hydrochloric acid were reacted to obtain 35 mg of the expected product identical to that of Example 11.

IR 1735 cm$^{-1}$ (17-keto); 1655 cm$^{-1}$ (conjugated ketone); 1633, 1614 cm$^{-1}$ (C=C).

NMR (CDCl$_3$, 250 MHz): 0.90 (s, 18 Md); 2.38 (s, SMe); 5.56 (m, H11); 5.83 (d, H4).

EXAMPLE 31
10β-[2-(methylthio)-ethyl]-Δ$^{9(11)}$-estren-3,17-dione

At 31 78° C., 136 mg of powdered lithium were introduced into 70 ml of liquid ammonia and then 500 mg of the product of Example 1 are added. The mixture was stirred for 3 and a half hours at −78° C. and the ammonia was evaporated off at ambient temperature. A saturated aqueous solution of ammonium chloride was added, and extraction was carried out with ethyl acetate. The extracts were chromatographed under pressure (eluant: cyclohexane-ethyl acetate 8-2 then 6-4) to obtain 138.5 mg of the expected product.

IR (CHCl$_3$): Absence of delta-4-3-one; 1734 cm$^{-1}$ (ketone in position 17); 1710 cm$^{-1}$ (ketone in position 3).

NMR (CDCl$_3$, 300 MHz): 0.86 (s, 18 Me); 2.13 (s, SMe); 5.42 (m, H11).

EXAMPLE 32
10β-[2-(methylthio)-ethyl]-5β-Δ$^{9(11)}$-restren-3,17-dione 400 mg of the product of Example 1 in 8 ml of methylethyl pyridine were hydrogenated for 2 hours under a pressure of 1200 mbars in the presence of 500 mg of barium sulfate with 10% of palladium. After filtering, 200 ml of methylene chloride and 100 ml of concentrated hydrochloric acid in 200 ml of water were added to filtrate. The organic phase was separated and dried and the solvents were eliminated under reduced pressure at 25° C. The residue was chromatographed on silica (eluant: ethyl acetate-cyclohexane 3-7) to obtain 300 mg of crude product which was crystallized from ether to obtain 130 mg of the expected product melting at 70° C.

NMR (CDCl$_3$, 300 MHz): 0.86 (s, 18 Me); 2.10 (s, SMe); 5.60 (m, H11).

EXAMPLE 33
10β-[2-(methylthio)-ethyl]-3-oxo-Δ$^{4,9(11)}$-estradien-17β-yl propanoate 500 mg of the product of Example 13 in 5 ml of dichloromethane were cooled to about 0° C. under an inert atmosphere and 500 microliters of triethylamine were added. Then, 250 microliters of propionyl chloride were added dropwise. After stirring for one hour, 50 ml of a saturated aqueous solution of ammonium chloride were added. Extraction was carried out with dichloromethane and the solvents were eliminated under reduced pressure. The residue was chromatographed on silica (eluant: ethyl acetate-cyclohexane 3-7) to obtain 480 mg of the expected product.

NMR (CDCl$_3$, 300 MHz): 0.79 (s, 18 Me); 1.15 and 2.34 (t and q COCH$_2$CH$_3$); 2.10 (s, Sme); 4.72 (t, H17); 5.49 (m, H11); 5.79 (d, H4).

EXAMPLE 34
10β-[2-(methylthio)-ethyl]-Δ$^{4,9(11)}$-estradien-3-one-17β-yl hexanoate Using the procedure of Example 33, 350 mg of the product of Example 13, 154 microliters of triethylamine and 154 microliters of caproyl chloride were reacted to obtain 280 mg of the expected product.

NMR (CDCl$_3$, 300 MHz): 0.79 (s, 18 Me); 0.91 (CH$_3$—CH$_2$ mask); 134 (m, CH$_2$); 2.10 (s, SMe); 2.31 (t, COCH$_2$; 4.70 (m, H17); 5.49 (m, H11); 5.79 (d, H4).

EXAMPLE 35
10β-[2-(2-propynylthio)-ethyl]-Δ$^{4,9(11)}$-estradien-3,17-dione

STEP A:
3,17-bis-(ethylendioxy)-10β-[2-(2-propynylthio)-ethyl]-Δ$^{4,9(11)}$-estradiene 800 mg of the product of Example 6 Step A in 4 ml of tetrahydrofuran in the presence of 0.39 ml of tetramethylethylenediamine was cooled to −78° C. and 2.25 ml of butyllithium were added, followed by stirring for 30 minutes 0.2 ml of propynyl bromide were added, followed by stirring for one and a half hours at −78° C. A saturated aqueous solution of ammonium chloride was added and extraction was carried out with methylene chloride. The extracts were dried and the solvents were eliminated under reduced pressure. After purification by chromatography on silica (eluant: cyclohexane-ethyl acetate 8-2), 462 mg of the expected product were recovered.

IR (CHCl$_3$): 3307, 2105 cm$^{-1}$ (—C≡CH)

STEP B:
10β-[2-(2-propynylthio)-ethyl]-Δ$^{4,9(11)}$-estradiene-3,17-dione

Using the procedure of Step B of Example 19, 460 mg of the product of Step A in 10 ml of ethanol and 2 ml of 6N hydrochloric acid were reacted to obtain 265 mg of the expected product.

IR (CHCl$_3$): 3307 cm$^{-1}$ (—C≡CH); 1735 cm$^{-1}$ (17-keto); 1665 cm$^{-1}$ (conjugated ketone); 1630, 1608 cm$^{-1}$ (C=C).

NMR (CDCl$_3$, 300 MHz): 0.90 (s, 18 Me); 2.23 (t, J=2.5 C≡CH); 3.26 (m, S—CH$_2$—C≡); 5.58 (m,H11); 5.82 (d, H4).

EXAMPLE 36
17-methylene-10β-[2-(methylthio)-ethyl]-Δ$^{4,9(11)}$-estradien-3-one

STEP A:
3-ethoxy-17-methylene-10β-[2-(methylthio)-ethyl]-Δ$^{4,9(11)}$-estradiene 6.5 ml of ethyl orthoformate were added under an inert atmosphere to 3 g of the product of Example 1 in 9 ml of ethanol and the mixture was heated to 70° C. 4 mg of p-toluene sulfonic acid in solution in 1 ml of ethanol were added, followed by stirring for a few minutes, and then the addition of 500 microliters of triethylamine. After cooling, 100 ml of methylene chloride were added and the mixture was washed with a saturated aqueous solution of ammonium chloride. The organic phase was dried and the solvent was eliminated under reduced pressure. After chromatography on silica (eluant: cyclohexane-ethyl acetate 9-1 with 1% triethylamine), 2.6 g of the expected product were obtained which was used as is for the following step.

STEP B:
17-methylene-10β-[2-(methylthio)-ethyl-Δ$^{4,9(11)}$-estradien-3-one 1.5 g of triphenylmethylphosphonium bromide was mixed under an inert atmosphere with 50 ml of dioxane and 227 mg of sodium methoxide were added. After stirring for one and a half hours at ambient temperature, 500 mg of the product of Step A dissolved in 2 ml of dioxane were added slowly. The mixture was heated for 3 hours at 70° C. and 100 ml of a saturated aqueous solution of sodium bicarbonate were added. Extraction was carried out with methylene chloride, and the extracts were dried and the solvents were eliminated under reduced pressure. 50 ml of 2N hydrochloric acid and 50 ml of ethanol were added followed by stirring for one hour, neutralizing with sodium hydroxide and extracting with methylene chloride. The extracts were dried and the solvent was eliminated under reduced pressure to obtain 830 mg of residue which was purified by chromatography on silica (eluant: ethyl acetate-cyclohexane 3-7) to obtain 320 mg of the expected product.

IR: little or no ketone in position 17; 1663 cm$^{-1}$ (conjugated ketone); 1632, 1612 cm$^{-1}$ (C=C).

NMR (CDCl$_3$, 300 MHz): 0.80 (s, 18 Me); 21.0 (s, Sme); 4.70 and 4.74 (m and M C=CH$_2$); 5.56 (m, H11); 8.80 (s, H4).

EXAMPLE 37
17α-methyl-10β-[2-(methylthio)-ethyl]-Δ$^{4,9(11)}$-estradien-17β-ol-3-one 300 mg of the product of Step A of Example 36 were mixed under an inert atmosphere with 10 ml of tetrahydrofuran and the mixture was cooled to −78° C. 1 ml of a solution of methyllithium (1.6M) in ether was added and the mixture was allowed to return to ambient temperature. The mixture was stirred for 16 hours and 50 ml of 2N hydrochloric acid were added followed by stirring for 2 hours and extraction with methylene chloride after having neutralized with sodium hydroxide. The organic phase was dried and the solvents were evaporated off. The residue was chromatographed on silica (eluant: cyclohexane-ethyl acetate 7-3) to obtain 100 mg of the expected product which was crystallized from ether.

NMR (CDCl$_3$, 300 MHz): 0.85 (s, 18 Me); 1.23 (s, 17α Me); 2.10 (s, SMe); 5.56 (m, H11); 5.79 (s, H4)

EXAMPLE 38
10β-[2-(methylthio)-ethyl]-spiro-(Δ$^{4,6,9(11)}$-estratrien-17β-,2α-oxiran-3-one 480 mg of sodium hydride in 10 ml of dimethylsulfoxide were heated to 50° C. for one hour and 10 ml of tetrahydrofuran were added, followed by cooling to 0° C. 2.04 g of trimethylsulfonium sulfonium iodide were added and the mixture was stirred for 20 minutes. 300 mg of the product of Step A of Example 36 dissolved in 5 ml of tetrahydrofuran were then added and the mixture was allowed to return to ambient temperature. After stirring for 3 hours, a saturated solution of sodium bicarbonate was added and extraction was carried out with methylene chloride. The extracts were dried and the solvents were eliminated under reduced pressure at 25° C. The residue was chromatographed on silica (eluant:ethyl acetate-cyclohexane 3-7) to obtain 380 mg of intermediate product containing a 17-epoxide and a protected 3-keto function in the form of enol ether.

450 mg of the product are stirred for 10 minutes in 7 ml of acetone and 350 microliters of water. 640 mg of chloranile were added and the mixture was stirred for 16 hours at ambient temperature. 100 ml of 2N sodium hydroxide were added after which the mixture was stirred for 30 minutes, followed by filtering and extraction with methylene chloride. The extracts were dried and the solvents were eliminated under reduced pressure at 25° C. The 410 mg of residue were chromatographed (eluant:ethyl acetate-cyclohexane 3-7 then 2-8) to obtain 110 mg of the expected product.

IR (CHCl$_3$): 1660, 1662, 1583, 877 cm$^{-1}$ (delta 4,6,3-one); 855, 917 cm$^{-1}$ (probable epoxide).

NMR (CDCl$_3$, 300 MHz): 0.95 (s, 18 Me); 2.10 (s, SMe); 2.69 and 2.93 (d, J=5 CH$_2$O epoxide); 2.83 (large H8); 5.83 (m, H11); 5.74 (s, H4); 6.18 (H6 and H11).

EXAMPLE 39
17-(fluoromethylene)-10β-[2-(methylthio)-ethyl]-Δ$^{4,9(11)}$-estradien-3-one 3.2 g of fluoromethyltriphenylphosphonium tetrafluoroborate in 15 ml of tetrahydrofuran were cooled to −78° C. and then 7 ml of butyllithium (1.2M) were added dropwise followed by stirring for 45 minutes. 750 mg of the product of Step A of Example 36 dissolved in 5 ml of tetrahydrofuran were added, and the mixture was stirred for 3 hours at −78° C. and for 16 hours at −20° C. The reaction medium was poured into 100 ml of a saturated aqueous solution of sodium bicarbonate and extracted with methylene chloride. The extracted were dried and the solvent was eliminated under reduced pressure at ambient temperature to obtain 3.55 g of intermediate product. The product was taken up in 100 ml of a 2N solution of hydrochloric acid and 100 ml of ethanol, followed by stirring for one hour, and extraction with methylene chloride, after having neutralized with sodium hydroxide. The organic phases were dried, and the solvent was eliminated under reduced pressure. The residue was chromatographed on silica (eluant: ethyl acetate-cyclohexane 3-7) to obtain 140 mg of the expected product.

NMR (CDCl$_3$, 300 MHz): Mixture of 2 isomers (50-50) 0.85 (d), 0.91 (s, 18 Me); 2.10 and 2.09 (s, SMe); 5.53 (m, H11); 5.80 (s, H4); 6.10 (d, t, J=85 H3, other ethylenics).

EXAMPLE 40
3-(fluoromethylene)-10β-[2-(methylthio)-ethyl]-Δ$^{4,9(11)}$-estradien-17-one and
3,17-bis-(fluoromethylene)-10β-[2-(methylthio)-ethyl]-Δ$^{4,9(11)}$-estradiene Using the procedure of Example 39, 5.55 g of fluoromethyltriphenylphosphonium tetrafluoroborate, 12.11 ml of butyllithium (1.2M) and 500 mg of the product of Example 1 were reacted with stirring for only one and a half hours at −78° C. The mixture was allowed to return to ambient temperature and water was added. Extraction was carried out with methylene chloride and the extracts were dried. The solvent was eliminated and the residue was chromatographed under pressure (cyclohexane-ethyl acetate 9-1) to obtain 165 mg of product A (3,17-bis-fluoromethylene) Rf=0.59, and 24.1 mg of product B (3-fluoromethylene) Rf=0.16.

Product A

IR (CHCl$_3$) 1734 cm$^{-1}$ (17-keto); 1622, 1629, 1614 cm$^{-1}$ (C=C).

NMR (CDCl$_3$, 300 MHz) 0.86 (s, 18 Me; 2.08 (s, SMe); 5.47 (m, H11); 5.66 (s, 1) 6.21 (s, 1) (resolved H4); 6.57 and 6.35 (d, J=84.5 H3, other ethylenics).

Product B

Ir Absence of (C=O); 1691, 1662, 1633, 1618 cm$^{-1}$ (C=C).

NMR (CDCl$_3$, 300 MHz) 0.83 and 0.89 (s, 18 Me); 2.08 (resolved s, SMe); 5.46 (m, H11); 5.64 and 6.31 (d, J=85 H31, H3); 6.57 (d, J=84.5 H3, H17).

EXAMPLE 41

3-(difluoromethylene)-10β-[2-(methylthio)-ethyl]-Δ$^{4,9(11)}$-estradien-17-one 4 g of the product of Example 1 in 9 ml of triglyme were cooled to 0° C. and 1.05 ml of dibromo difluoromethane. Then 6.3 ml of hexamethylphosphotriamide were added and after stirring for one hour at 0° C., the mixture was allowed to return to ambient temperature. The mixture was stirred for 20 hours and filtered. The filtrate was concentrated and chromatographed under pressure. The residual triglyme was eliminated under reduced pressure to obtain 180 mg of crude product which was purified by chromatography on silica (eluant: cyclohexane-ethyl acetate 9-1) to obtain the expected product with an Rf=0.77.

NMR (CDCl$_3$, 300 MHz): 0.86 (s, 18 Me): 2.09 (s, SMe); 5.47 (m, H11); 5.84 (s1, H4).

EXAMPLES: PHARMACEUTICAL COMPOSITIONS

Tablets were prepared containing 50 mg of the product of Example 1 and sufficient excipient of talc, starch, magnesium stearate for a tablet of 120 mg.

PHARMACOLOGICAL STUDY

A) Study In Vitro

Inhibition dependent on the concentration (measurement of the IC$_{50}$=concentration of the inhibitor necessary to reduce the enzymatic activity by 50%).

Human placentas were used which were washed one hour at most after delivery, perfused with physiological serum (5 liters) via the umbilical vein and then deep-frozen at −40° C.

1) Obtaining the Placental Microsomes

The placentas were thawed at 4° C. and then homogenized (1:3) in a 10 mM phosphate buffer, pH=7.0 containing 100 millimoles of potassium chloride (KCl), 10 millimoles of dithiothreitol (DTT), 10 millimoles of ethylenediamine-tetraacetic acid (EDTA), 40 millimoles of nicotinamide and 250 millimoles of sucrose. The homogenates were then subjected to different phases of centrifugation until the "9000 g" supernatant was obtained (corresponding to cytosol and to endoplasmic reticulum). This supernatant was then subjected to an ultra-centrifugation stage (90 minutes, 150,000 g) to obtain the microsomal deposit. The microsomes were then resuspended in a 50 mM phosphate buffer, pH=7.4, containing 100 millimoles KCl, 1 millimole EDTA, 1 millimole DTT and glycerol (10%). The microsomal suspension was aliquoted and the fractions deep-frozen at the temperature of liquid nitrogen. The concentration of proteins in the microsomal suspension was determined by the BRADFORD method (BRADFORD., Anal. Biochem., Vol. 72, (1976) 248).

2) Measurement of the CI$_{50}$ of Each Inhibitor

To 960 microliters of phosphate buffer (50 millimoles, pH=7.2) 2.5 millimoles glucose-6-phosphate, and containing 0.16 international units of glucose-6-phosphate dehydrogenase (G-6-PDH), the following were added in this order:

1) −10 microliters of inhibitor solubilized in dimethyl-sulfoxide (DMSO) to give final concentrations from 10$^{-5}$M to 10$^{-10}$M.

2) −10 microliters of substrate which was 500 nM Androstenedione solubilized in ethanol and containing 1β,- 2β-(H$^3$)-Androstenedione in a known isotopic dilution (approx. 200,000 disintegrations per minute).

3) 10 microliters of microsomal suspension equivalent to 25 micrograms of proteins per test.

The enzymatic reaction was then very rapidly initiated by the addition of 10 microliters of reduced nicotinamide adenine dinucleotide phosphate (NADPH) solubilized in water. After stirring, each test was incubated at 37° C. for 10 minutes. The reaction was then stopped by the addition of chloroform (4 ml).

After vigorous stirring of the tubes, they were decanted and centrifuged at 4° C. for 10 minutes at a speed of 3000 r.p.m. (rotations per minute), that is 600 X g. After centrifuging, and for each tube, 100 microliters of supernatant was removed and counted in the presence of a scintillating liquid. This method was derived from the procedures described by Reed et al, (J. Biol. Chem., Vol. 251, (1976), p. 1625) and Thompson et al, (J. Biol. Chem., Vol. 249, (1974), p. 5364). The enzymatic activity (aromatase) was proportional to the percentage of tritium salted out in the form of tritiated water (H$^3$20) in the course of the reaction. The inhibition obtained for each concentration of each inhibiting product of the invention was calculated as a percentage of the controls (arbitrary 100%, obtained in the absence of any inhibitor). The CI$_{50}$ was equal to the concentration of inhibitor necessary to decrease the enzymatic activity by 50% and the values of the CI$_{50}$'s obtained for the inhibiting products of the invention are as follows:

| Product of example | CI$_{50}$ |
| --- | --- |
| 1 | 2 × 10$^{-8}$ M |
| 2 | 8.7 × 10$^{-7}$ M |
| 13 | 5 × 10$^{-8}$ M |
| 21 | 3.3 × 10$^{-7}$ M |
| 22 | 5 × 10$^{-7}$ M |
| 26 (3 beta OH) | 1.65 × 10$^{-7}$ M |
| 31 | 5.5 × 10$^{-9}$ M |

B) Study In Vivo

I-AMOUNT OF ESTRADIOL CIRCULATING IN RATS INDUCED WITH P.M.S.G.

(Pregnant Mare Serum Gonadotrophine)

Female rats weighing 150 g were induced by an injection of P.M.S.G. (100 I.U./rat/sc). After 90 hours, the animals were treated with the product under test (sc or po) and a blood sample was taken before and after treatment to measure the amount of seric estradiol.

Protocol

D0, −90 h: injection of 100 I.U. of PMSG/rat.

DO, 0 h: sample of blood from choroid plexus then treatment with the product under test.
DO, +2 h: sample of blood.
DO, +6 h: killing of animals and collection of blood.

Dosage

After coagulation and centrifugation of the blood, the serum was recovered which was dosed with estradiol (E2) by means of an RIA dosage kit (Baxter ER155). The results were expressed as a percentage variation relative to the amount of estradiol at time 0 (each animal is its own control). The statistical test used is the Mann-Whitney U-test (*:$p<0.05$; **:$p<0.01$).

| Product of Example | Subcutaneously | | | Parenterally | | |
|---|---|---|---|---|---|---|
| | DOSE mg/kg | +2 h | +6 h | DOSE mg/kg | +2 h | +6 h |
| 1 | 1 | −55** | −68** | 5 | −51** | −51** |
| 13 | 1 | −56** | −60** | 5 | −70** | −53** |
| 26 | | | | 5 | −53** | −53** |
| 3 alpha OH 26 | | | | 5 | −63** | −64** |
| 3 beta OH 27 | 1 | −56** | −20** | 5 | −58** | −45** |
| 31 | | | | 5 | −69** | −56** |

II-AMOUNT OF ESTRADIOL IN A MACAQUE CYNOMOLGUS MONKEY PROTOCOL

1) Animals Used

In this test, female macaque cynomolgue monkeys weighing 3 to 5 kg were used. The animals were treated between days 8 and 10 of the menstrual cycle at a rate of 1 mg/kg of the product of Example 1 by sub-cutaneous route with a single injection.
Time 0 h: Blood sample, then treatment.
30 min: Blood sample.
1 h 30: Blood sample.
2 h: Blood sample.

The estradiol in the blood that was recovered was dosed on EDTA with, and dosages were carried out on the plasma (RIA) The injection of the product of Example 1 at a dose of 1 mg/kg sub-cutaneously caused a lowering of the estradiol by approximately 42 to 75% after 2 hours.

Various modifications of the compounds and methods of the invention may be made without departing from the spirit or scope thereof and it is to be understood that the invention is intended to be limited only as defined in the appended claims.

What is claimed is:
1. A compound selected from the group consisting of a compound of the formula

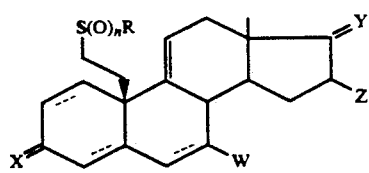

wherein R is selected from the group consisting of hydrogen, alkyl, alkylthio and haloalkyl of 1 to 6 carbon atoms, alkenyl and alkynyl of 2 to 6 carbon atoms, arylthio of 6 to 10 carbon atoms, optionally substituted with at least one amino or nitro, hydrocarbyl aryl of 6 to 12 carbon atoms, acyl of an organic carboxylic acid of 1 to 12 carbon atoms, —CN, cycloalkyl of 3 to 6 carbon atoms and —(CH$_2$)$_m$—Re, m is an integer from 1 to 3, Re is —OH or —SH or —SAlk, Alk is alkyl of 1 to 6 carbon atoms, X is selected from the group consisting of O, N—OR$_1$,

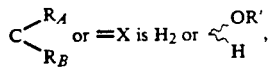

R$_A$ and R$_B$ are individually selected from the group consisting of hydrogen, halogen and alkyl of 1 to 6 carbon atoms, R$_1$ is hydrogen or alkyl of 1 to 6 carbon atoms, R' is hydrogen or acyl of an aliphatic carboxylic acid of 1 to 12 carbon atoms, the wavy lines indicate α- or β-position, Y is selected from the group consisting of O, NOR$_1$, or =Y is

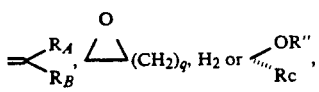

q is an integer from 1 to 3, Rc is selected from the group consisting of hydrogen, alkyl of 1 to 6 carbon atoms and alkenyl and alkynyl of 2 to 6 carbon atoms, R'' is hydrogen or acyl of an aliphatic carboxylic acid of 1 to 12 carbon atoms, W is selected from the group consisting of hydrogen, optionally substituted alkyl and alkylthio of 1 to 6 carbon atoms arylthio of 6 to 10 carbon atoms optionally substituted with at least one amino or nitro, Z is hydrogen or alkyl of 1 to 10 carbon atoms, n is an integer from 0 to 2, the dotted lines in 1(2)-, 4(5)- and 6(7)-position indicate an optional double bond between the carbon atoms and their non-toxic, pharmaceutically acceptable salts.

2. A compound of claim 1 having the formula

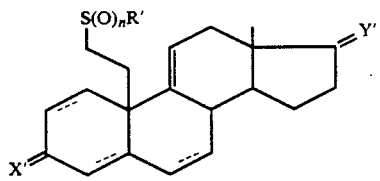

wherein R' is selected from the group consisting of alkyl, alkylthio and haloalkyl of 1 to 4 carbon atoms, alkenyl and alkynyl of 2 to 4 carbon atoms, —CN and acyl of an aliphatic carboxylic acid of 1 to 4 carbon atoms, X' is selected from the group consisting of O, CH$_2$, NOR$_1$ or =X' is

R'$_1$ is hydrogen or alkyl of 1 to 4 carbon atoms, Y' is 0 or =Y'

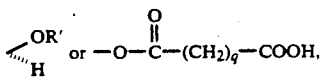

R' is hydrogen or acyl of an alkanoic acid of 1 to 12 carbon atoms and n, q and the dotted lines have the definition of claim 1.

3. A compound of claim 2 wherein X' is 0 or =X' is

and R' is selected from the group consisting of alkyl and haloalkyl of 1 to 4 carbon atoms and alkenyl and alkynyl of 2 to 4 carbon atoms.

4. A compound of claim 1 selected from the group consisting of 10β-[2-(methylthio)-ethyl]-Δ$^{4,9(11)}$-estradiene-3,17-dione; 10β-[2-(ethylthio)-ethyl]-Δ$^{4,9(11)}$-estradiene-3,17-dione; 10β-[2-(methylthio)-ethyl]-Δ$^{4,9(11)}$-estradiene-17β-ol-3-one; 10β-[2-(ethenylthio)-ethyl]-Δ$^{4,9(11)}$-estradiene-3,17-dione; 10β-[2-(ethynylthio)-ethyl]-Δ$^{4,9(11)}$-estradiene-3,17-dione; 10β-[2-(fluoromethylthio)-ethyl]-Δ$^{4,9(11)}$-estradiene-3,17-dione, the butane dioate of 10β-[2-(methylthio)-ethyl]-Δ$^{4,9(11)}$-estradien-3-one-17β-yl and of sodium; 10β-[2-methylthio)-ethyl]-Δ$^{4,9(11)}$-estradiene-3β,17β-diol; 10β-[2-(methylthio)-ethyl-Δ$^{4,9(11)}$-estradiene-3α,17β-diol and 10β-[2-(methylthio)-ethyl-Δ$^{4,9(11)}$-estradiene-3,17-dione.

5. A composition of cytochrome P450 aromatase specific activity comprising an effective aromatase specific amount of at least one compound of claim 1 and an inert pharmaceutical carrier.

6. A composition of claim 5 comprising an activate ingredient having the formula

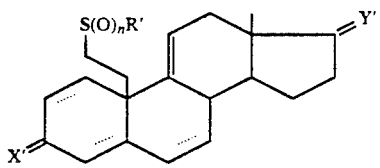

wherein R' is selected from the group consisting of alkyl, alkylthio and haloalkyl of 1 to 4 carbon atoms, alkenyl and alkynyl of 2 to 4 carbon atoms, —CN and acyl of an aliphatic carboxylic acid of 1 to 4 carbon atoms, X' is selected from the group consisting of O, CH$_2$, NOR$_1$ and =X' is

R$_1$ is hydrogen, or alkyl of 1 to 4 carbon atoms, Y' is O or =Y' is

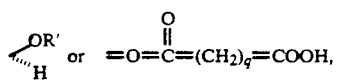

R' is hydrogen or acyl of an alkanoic acid of 1 to 12 carbon atoms and n, q and the dotted lines have the definition of claim 1.

7. A composition of claim 5 wherein X is 0 or =X is

and R' is selected from the group consisting of alkyl and haloalkyl of 1 to 4 carbon atoms and alkenyl and alkynyl of 2 to 4 carbon atoms.

8. A composition of claim 5 wherein the active compound is selected from the group consisting of 10β-[2-(methylthio)-ethyl]-Δ$^{4,9(11)}$-estradiene-3,17-dione; 10β-[2-(ethylthio)-ethyl]-Δ$^{4,9(11)}$-estradiene-3,17-dione; 10β-[2-(methylthio)-ethyl]-Δ$^{4,9(11)}$-estradiene-17β-ol-3-one; 10β-[2-(ethenylthio)-ethyl]-Δ$^{4,9(11)}$-estradiene-3,17-dione; 10β-[2-(ethynylthio)-ethyl]-Δ$^{4,9(11)}$-estradiene-3,17-dione; 10β-[2-(fluoromethylthio)-ethyl]-Δ$^{4,9(11)}$-estradiene-3,17-dione, the butane dioate of 10β-[2-(methylthio)ethyl]-Δ$^{4,9(11)}$-estradiene-3-one-17β-yl and of sodium, 10β-[2-(methylthio)-ethyl]-Δ$^{4,9(11)}$-estradiene-3β,17β-diol; 10β-[2-(methylthio)-ethyl-Δ$^{4,9(11)}$-estradiene-3α,17β-diol and 10β-[2-(methylthio)-ethyl-Δ$^{4,9(11)}$-estradiene-3,17-dione.

9. A method of inducing cytochrome P450 aromatase specific activity in warm-blooded animals comprising administering to warm-blooded animals an effective amount of a compound of claim 1 sufficient to induce aromatase specific activity.

10. A method of claim 9 wherein the active compound has the formula

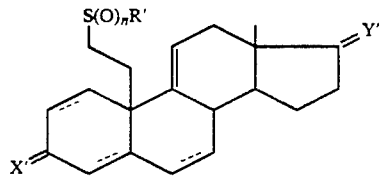

wherein R' is selected from the group consisting of alkyl, alkylthio and haloalyl of 1 to 4 carbon atoms, alkenyl and alkynyl of 2 to 4 carbon atoms, —CN and acyl of an aliphatic carboxylic acid of 1 to 4 carbon atoms, X' is selected from the group consisting of O, CH$_2$, NOR$_1$ or =X' is

R$_1$ is hydrogen or alkyl of 1 to 4 carbon atoms, Y' is O or =Y' is

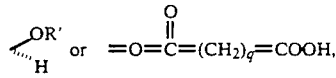

R' is hydrogen or acyl of an alkanoic acid of 1 to 12 carbon atoms and n, q and the dotted lines have the definition of claim 1.

11. A method of claim 9 wherein X is O or =X is

and R' is selected from the group consisting of alkyl and haloalkyl of 1 to 4 carbon atoms and alkenyl and alkynyl of 2 to 4 carbon atoms.

12. A method of claim 9 wherein the active compound is selected from the group consisting of 10β-[2-(methylthio)-ethyl]-Δ$^{4,9(11)}$-estradiene-3,17-dione; 10β-[2-(ethylthio)-ethyl]-Δ$^{4,9(11)}$-estradiene-3,17-dione; 10β-[2-(methylthio)-ethyl]-Δ$^{4,9(11)}$-estradiene-17β-ol-3-one; 10β-[2-(ethenylthio)-ethyl]-Δ$^{4,9(11)}$-estradiene-3,17-dione; 10β-[2-(ethynylthio)-ethyl]-Δ$^{4,9(11)}$-estradiene-3,17-dione; 10β-[2-(fluoromethylthio)-ethyl]-Δ$^{4,9(11)}$-estradiene-3,17-dione, the butane dioate of 10β-[2-(methylthio)ethyl]-Δ$^{4,9(11)}$-estradien-3-one-17β-yl and of sodium, 10β-[2-methylthio)-ethyl]-Δ$^{4,9(11)}$-estradiene-3β,17β-diol; 10⊕-[2-(methylthio)-ethyl-Δ$^{4,9(11)}$-estradiene-3α,17β-diol and 10β-[2-(methylthio)-ethyl-Δ$^{4,9(11)}$-estradiene-3,17-dione.

* * * * *